United States Patent [19]
Ortiz

[11] Patent Number: 5,441,494
[45] Date of Patent: Aug. 15, 1995

[54] MANIPULABLE HAND FOR LAPAROSCOPY

[75] Inventor: Mark Ortiz, Milford, Ohio

[73] Assignee: Ethicon, Inc., Somerville, N.J.

[21] Appl. No.: 99,675

[22] Filed: Jul. 29, 1993

[51] Int. Cl.6 .............................................. B25J 1/00
[52] U.S. Cl. ...................................... 606/1; 294/19.1; 606/205
[58] Field of Search .......................... 294/19.1, 22, 24; 606/1, 205; 604/280

[56] References Cited

U.S. PATENT DOCUMENTS

| | | | |
|---|---|---|---|
| 1,470,914 | 10/1923 | Day | 606/1 |
| 1,539,831 | 6/1925 | Day | 606/1 |
| 2,514,063 | 7/1950 | Hubbard | 294/19.1 |
| 2,694,603 | 11/1954 | Griffin | 294/19.1 X |
| 3,907,354 | 9/1975 | Ocampo | 294/19.1 |
| 3,937,512 | 2/1976 | Baughman | 294/19.1 |
| 4,760,848 | 8/1988 | Hasson | 294/19.1 X |
| 4,863,204 | 9/1989 | Peters | 294/19.1 |

*Primary Examiner*—Peter A. Aschenbrenner
*Attorney, Agent, or Firm*—Paul A. Coletti

[57] ABSTRACT

A manipulable hand for use in laparoscopic surgery is disclosed, having a master or control hand with clamps for attaching the master hand to that of an operator, the master hand having at least one finger, the finger having at least one hinge corresponding to an interphalangeal joint in a human hand. The manipulable hand further includes a slave or controlled hand, distally disposed from the operator, the slave hand having at least one finger, the finger having at least one hinge corresponding to an interphalangeal joint of a human finger. Both the master and slave hinges are capable of movement corresponding to flexion and extension of a human finger. The master hand and the slave hand are connected by motion transmission rods or cables, and the movements of the slave hand corresponds one-for-one to the movements of the master hand. The preferred embodiment of the manipulable hand has two fingers and a thumb, the thumb of both the master and slave hands is capable of movements corresponding to palmar adduction and abduction, and the fingers of both the master and slave hands are capable of coplanar spreading away from each other and moving back toward each other, moving from a substantially aligned position to a V-shaped configuration. The rods are enclosed within a hollow shaft, and the master and slave hands are mounted with parallel connections therebetween forming wrists at the ends of the shaft.

27 Claims, 11 Drawing Sheets

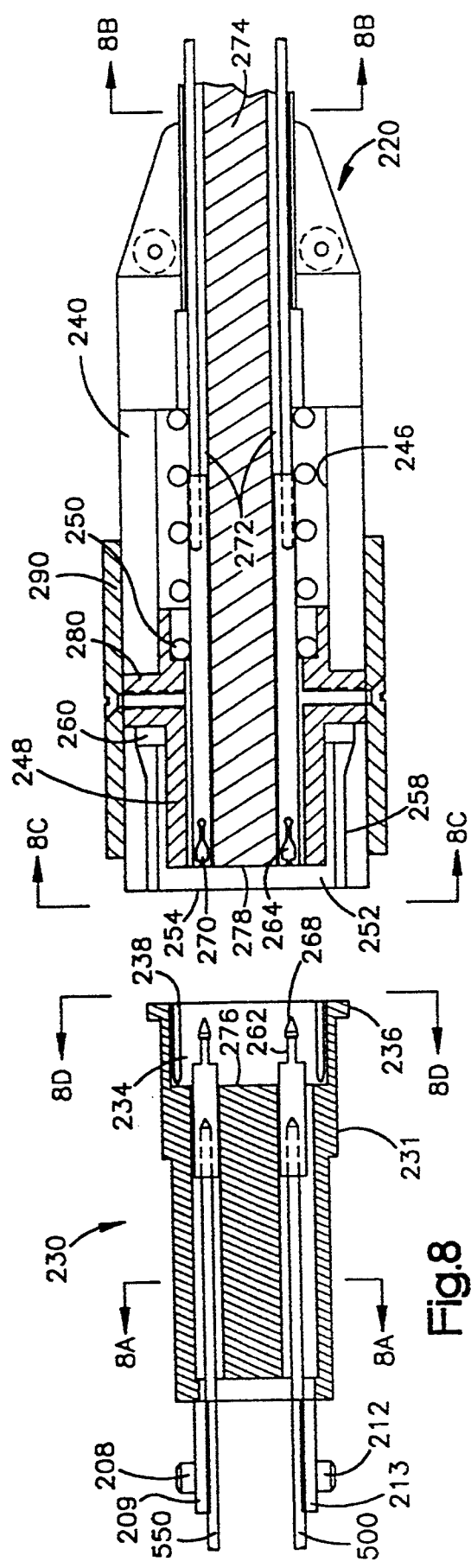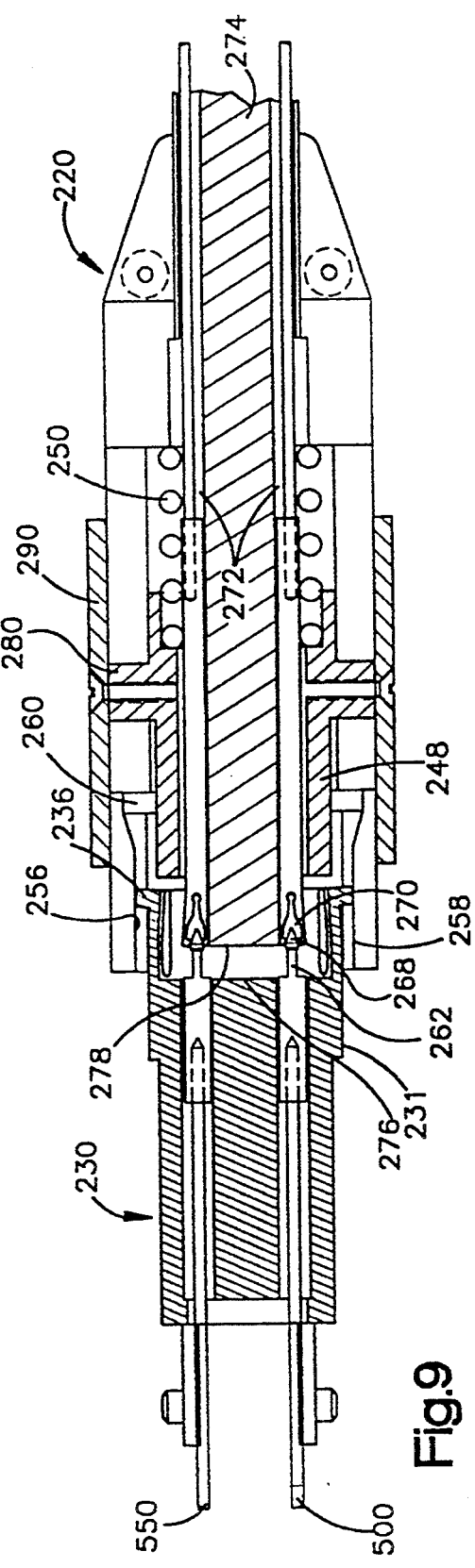

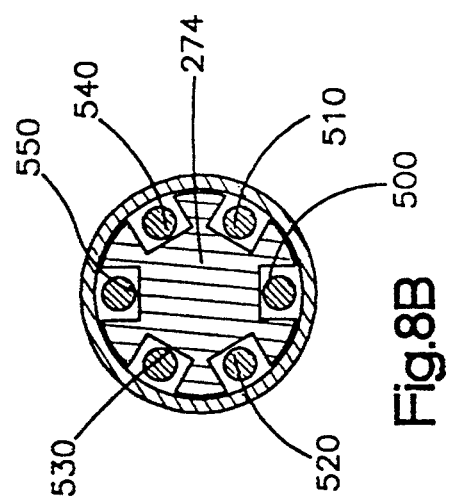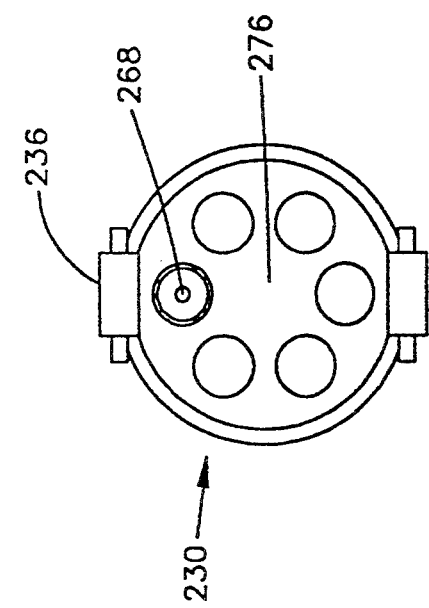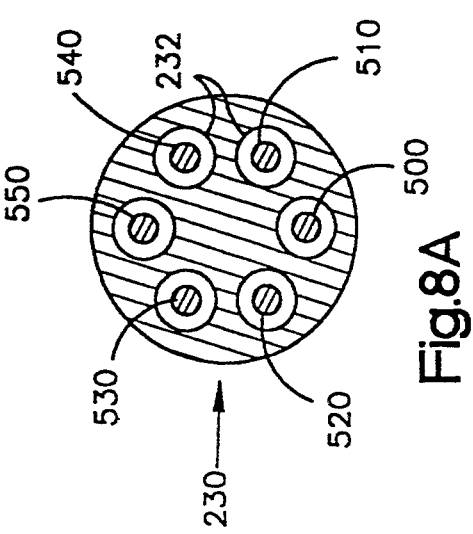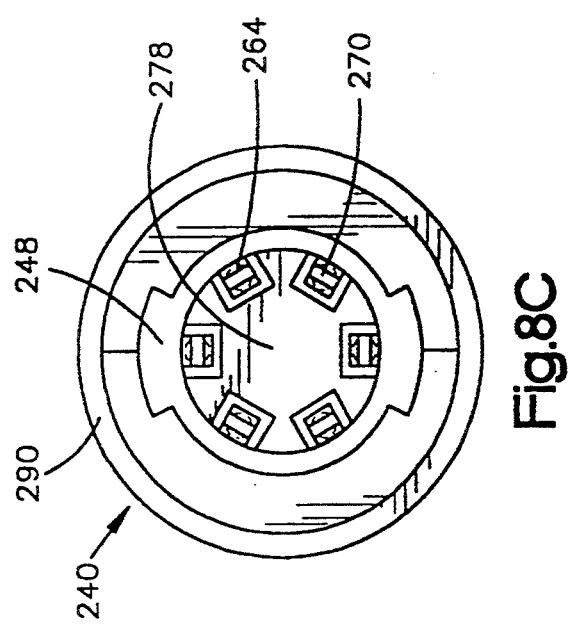

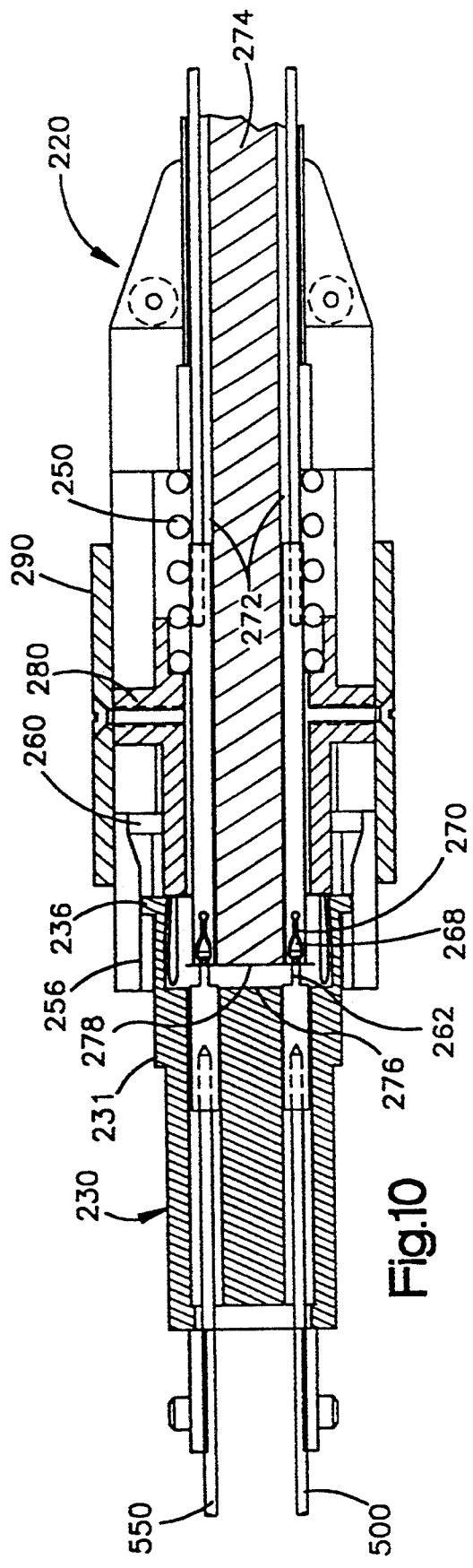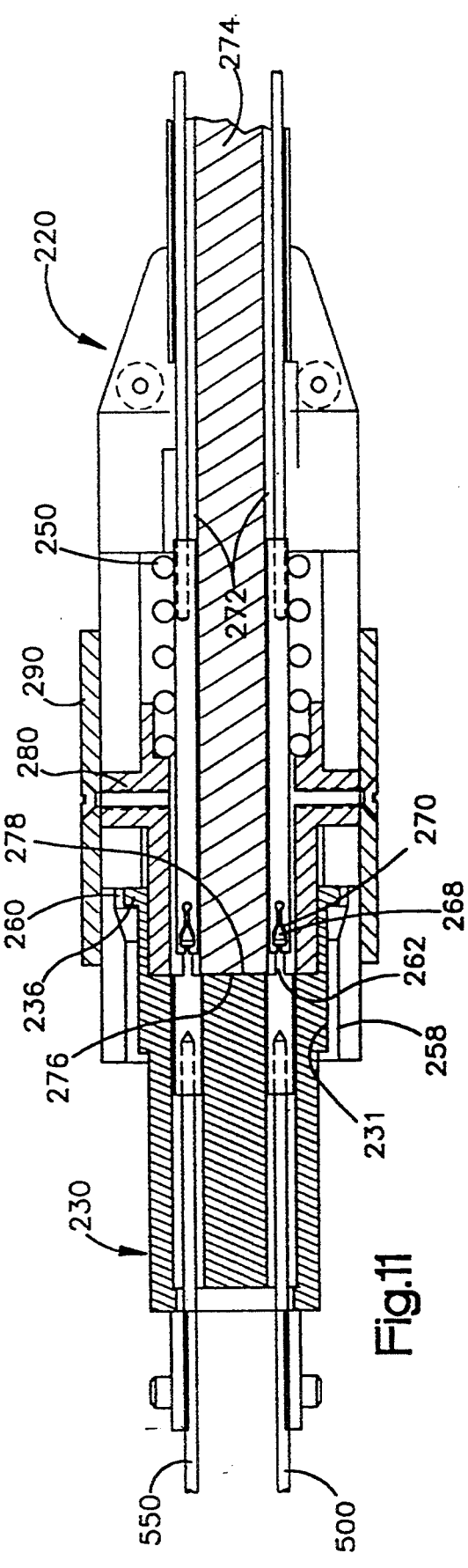

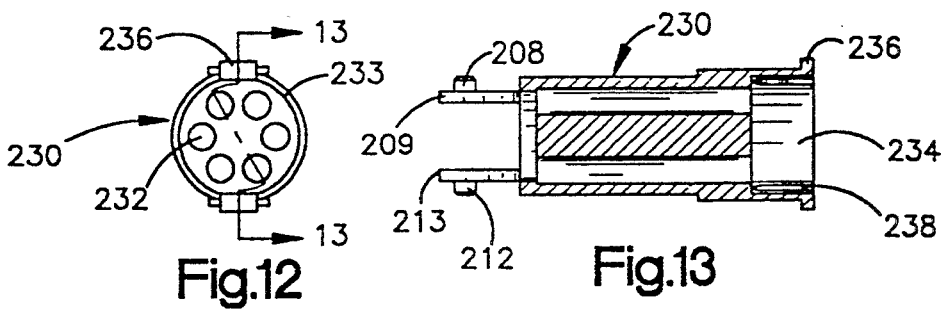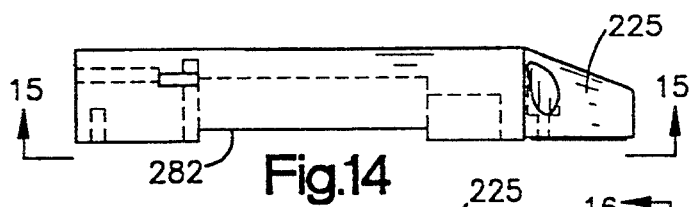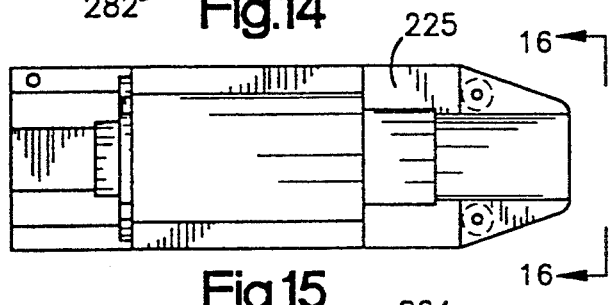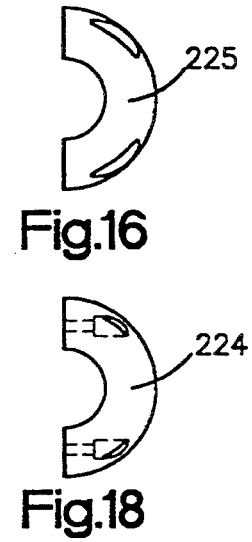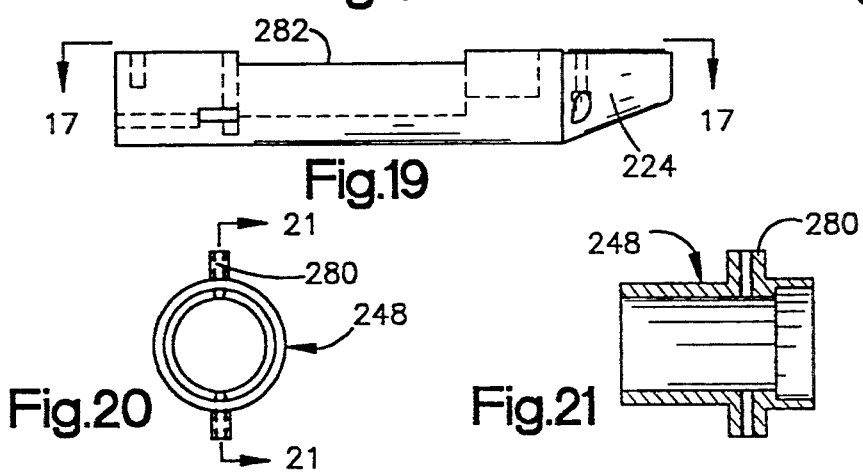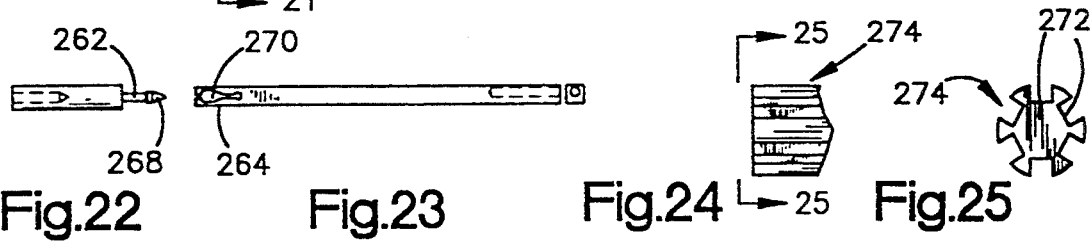

MANIPULABLE HAND FOR LAPAROSCOPY

BACKGROUND OF THE INVENTION

This invention relates to surgical instruments and, more particularly, to a manipulable hand for use in laparoscopic surgery.

Laparoscopic surgical techniques involve performing surgical procedures through a small diameter tube that is inserted through a small incision in the patient. These techniques minimize trauma to surrounding tissue and organs and greatly reduce the recovery period which, in many cases, is due to the size of the incision required to gain access to the surgical site. To perform these laparoscopic techniques, a small incision is made, and a small tube or cannula is inserted through the incision. The cannula constitutes a port through which various instruments can be inserted to perform procedures, such as cutting, suturing and removal of organs. These procedures involve far less trauma in the patient, less recovery time, and the ability to control medical costs generally by the elimination of large incisions on the patient's body.

Laparoscopic surgical techniques have essentially removed the surgeon's hands from the patient's body and replaced them with blades, suture needles, and small crude graspers. In many cases the surgeon needs better, more sensitive control, like that afforded by the human hand. Such control can be achieved by directly using the surgeon's skilled, highly trained hands. However, the purpose of laparoscopy is to reduce the trauma of surgery by making smaller incisions. Such smaller incisions are enabled by providing means by which the surgeon can observe the site of interest and means by which the surgeon may remotely perform his surgical function. Provision of these means avoids the necessity of large incisions due to the need to insert the surgeon's hands into the surgical incision.

In order to achieve the goals of laparoscopic surgery, the means provided as a substitute for the surgeon's hands should be as similar as possible to the real thing. The closest approximations presently in use are grasping devices of rather crude design, and devices capable only of cutting, scraping, or similar actions. All of these are rather primitive compared to the human hand wielding an appropriate surgical tool. Known laparoscopic techniques allow the surgeon only limited capabilities within the surgical site.

BRIEF DESCRIPTION OF THE INVENTION

The present invention overcomes the problem arising from the conflicting need for obtaining the benefits of skilled, delicate control of surgical procedures while simultaneously achieving the benefits of laparoscopic surgical techniques. The present invention allows substantial control by the surgeon's hands while at the same time avoiding the actual insertion of those hands into the patient's body.

According to the preferred embodiment of this invention, a manipulable, distally disposed controlled hand for laparoscopic surgery is provided having three slave digits, the digits comprising a thumb and two fingers. These digits are movably attached to a mounting base positioned upon the distal end of a shaft. The digits, the mounting base and a portion of the shaft are insertable through a cannula into a surgical incision. The proximal, or master, end of the shaft comprises a master or proximal control hand or "power glove", into which a human operator's thumb and two fingers may be inserted. The proximal control hand provides motion, power, and control from the operator's hand to the respective digits of the distal or controlled slave hand. Each digit of the master or control hand is mounted on a base attached to the tube connecting the master and slave hands. Each of the digits on the distal hand is connected and responsive to a homologous digit on the proximal hand, which is in turn operated by a homologous digit on the operator's hand. The digits of the master hand are hinged at points homologous to the interphalangeal joints of the human hand. Each section between the hinges of the master hand corresponds to the phalanges of the human hand. The distal or controlled slave hand comprises hinged sections corresponding and responsive to those of the master hand. Thus, the articulations of the controlled slave hand correspond to the articulations of the human operator's hand, allowing the slave hand to duplicate the actions and responses of the human hand as closely as possible.

At each end of the hollow shaft, adjacent both the proximal and the distal hands, the preferred embodiment of the present invention includes an articulated wrist, for providing wrist-like motion from the operator's hand to the wrist adjacent the distal hand.

The digits are in each case capable of motion independent of one another, and each is capable of flexion and extension. The fingers on both the distal and master hands are capable of spreading apart, i.e., moving horizontally away from and back toward each other, between a first substantially aligned position and a second, angularly related V-shaped position. The thumb is opposable to and is capable of spreading away from and moving toward the fingers, in motions known as palmar abduction and adduction, respectively. The thumb of the proximal control hand is attached to the base via an axis about which the thumb is laterally pivotable. This lateral freedom of movement allows the master thumb control to pivot from side to side, which provides for use of the same proximal control hand unit by both right- and left-handed operators.

The proximal control hand further comprises an adjustable palm plate by which the apparatus may be adjusted for varying hand sizes of different operators using the same manipulable hand. The combined elements of lateral adjustability of the thumb for handedness and of axial adjustability of the palm plate for hand size provide substantial flexibility in use of the manipulable hand by multiple operators. Such flexibility allows substantial cost savings to the user.

According to the present invention, all motions of the distal hand are directed by and mechanically controlled from the proximal control hand, and the operative connections, or motion transmission means, therebetween comprise rigid or flexible control rods or cables. Thus, there exists a one for one relationship in the movements of the master control hand and the controlled slave hand. Each movement of the control hand is transmitted to the controlled hand; although the movements may not be exactly duplicated, each movement of the control hand causes an associated movement of the controlled hand. The result of this one for one relationship is that when the master digit flexes, the slave digit flexes in response; however, while the master digit may move as if to curl around an object, the slave finger may only bend around the object to a degree sufficient to hold the object in a steady position. Thus, the distal hand is in a one for one relationship in the sense that, for each position of a master digit, there is one and only one responsive position of a corresponding slave digit, but the distal hand is not required to move in an exact 1::1 duplication of the master hand movement. Accordingly, in the embodiment described hereinbelow, the digits have only two phalanges, rather than three phalanges of the human hand. An embodiment having three phalanges on some or all digits is within the scope of the present invention.

The device of present invention is free of springs for returning digits to any particular or preset position. Thus, the operator meets no resistance due to spring tension seeking to return the mechanism to a particular rest position. As a result, the invention does not become an additional source of fatigue to the surgeon or operator during a surgical procedure.

Consistent with the purposes of laparoscopy, the distal hand is smaller than the human hand which it replaces. Its size may vary within a wide range, from a hand having fingers a few millimeters in length up to the largest hand commensurate with use in laparoscopy. Thus, the hand must be capable of passing through a laparoscopic cannula and into the laparoscopic surgical incision. This capability is preferably achieved by placing the fingers of the controlled slave hand into an aligned position in which the longitudinal axis of the distal hand has a minimum cross sectional diameter. In this configuration, the digits of the controlled hand are substantially parallel to each other, and are aligned with the axis of the shaft connecting the distal and proximal hands.

The requirements of the particular type of surgery and the individual surgeon or other operator will primarily determine the actual size of the distal hand employed in any particular procedure. The slave hand will have a size commensurate with the type and location of the surgical procedure.

The manipulable hand of the present invention is intended to be used with other known laparoscopic techniques. Of particular importance are visualization techniques, of great importance to laparoscopy, by which the surgeon visualizes the surgical site. The usual visualization techniques include the use of fiber optic illumination and video display, but may include other less direct methods such as fluorometry, X-ray, magnetic resonance imaging and computerized axial tomography.

One method of providing illumination for visualization is described in the commonly assigned application, U.S. Ser. No. 07/868,107, filed Apr. 14, 1992, which application is hereby incorporated herein by reference. That application describes an illuminated surgical cannula, comprising optical fibers embedded within the fiber composite body of the cannula. In that invention, illumination is externally provided to optical fibers integral to the body of the cannula. The integral fibers transmit the light into the incision and the surgical site. Illumination thus provided allows the operator to visualize the site by known laparoscopic methods, such as video transmission.

Near the proximal end of the shaft, but not limited to such position, the preferred embodiment of the present invention includes a quick release coupling means by which the distal portion of the apparatus may be coupled to or uncoupled from the proximal portion of the shaft. The coupling allows exchange of the distal hand for either a replacement distal hand or other laparoscopic instrument operable by the master hand. By means of a similar coupling device, each individual slave digit on the distal hand may itself comprise coupling means allowing for removal and replacement of individual digits.

In a further aspect of the present invention, the quick-release coupling means provides versatility of choice between reusable and disposable surgical instrumentation. The individually removable finger and thumb portions, or the entire distal hand portion, may be made of disposable material. When a portion is disposable the remainder may be sterilized for reuse. Thus, the capability of coupling and uncoupling allows the decision of which instruments are disposable or reusable to be based on both medical and economic considerations, rather than having medical decisions dictated solely by economic necessity.

BRIEF DESCRIPTION OF THE DRAWINGS

FIG. 8 is a cross sectional view of a coupling assembly according to this invention illustrating the assembly in an uncoupled condition;

FIG. 9 is a cross sectional view similar to FIG. 8 illustrating the coupling in a partially coupled condition;

FIG. 10 is a cross sectional view of the coupling assembly illustrating the coupling in a more advanced coupled condition;

FIG. 11 is a cross sectional view of the coupling assembly illustrating the assembly in a completely coupled condition; and FIGS. 12-25 are views of various elements of the coupling assembly illustrated in FIGS. 8-11.

DETAILED DESCRIPTION OF THE DRAWINGS

Figure 1:
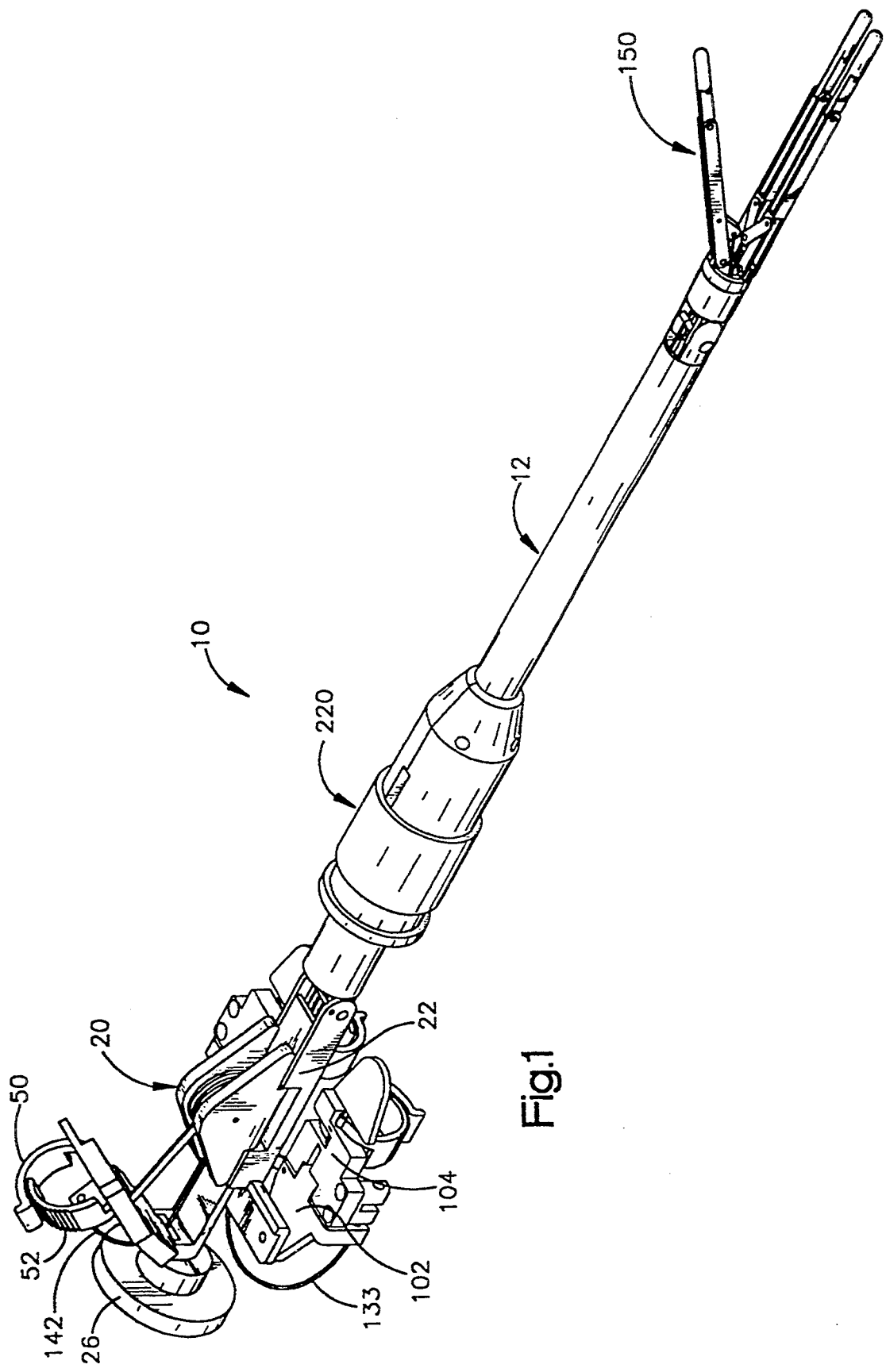
FIG. 1 is a perspective view of a manipulable surgical hand according to the invention.

With particular reference to FIGS. 1-4, a manipulable surgical hand 10 of the present invention includes a manipulable master, proximal or control hand 20, a slave, distal or controlled hand 150, and a hollow elongated tube or sleeve 12 which provides mounting bases for and connection between the control hand 20 and the controlled hand 150. The hollow sleeve 12 may optionally include a coupling 220. Motion transmission rods 500, 510, 520, 530, 540 and 550, which form the connection between operative portions of the master hand 20 and the slave hand 150, are carried within hollow tube 12.

In the following description, a certain standard orientation of the manipulable hand 20 is used in defining relative positions of the hand. The master hand 20 is considered for this purpose to have at least one finger and a thumb disposed thereon. In the standard orientation, the master or proximal hand is always considered to be at the proximal end, to the viewer's left as in FIGS. 1–4, and the thumb is always oriented upwards. Thus, for example, when considering an embodiment having two fingers and a thumb, one finger will always be "left" and the other will always be "right." The standard orientation is for descriptive purposes only; the manipulable surgical hand 10 can, of course, be operated in any orientation.

The master hand 20 is designed to be releasably attached to and controlled by a human operator's hand. Each digit of hand 20 includes clamps for securely but releasably holding the fingers of the human hand. The clamps used in the present invention will be further described below.

Figure 5:
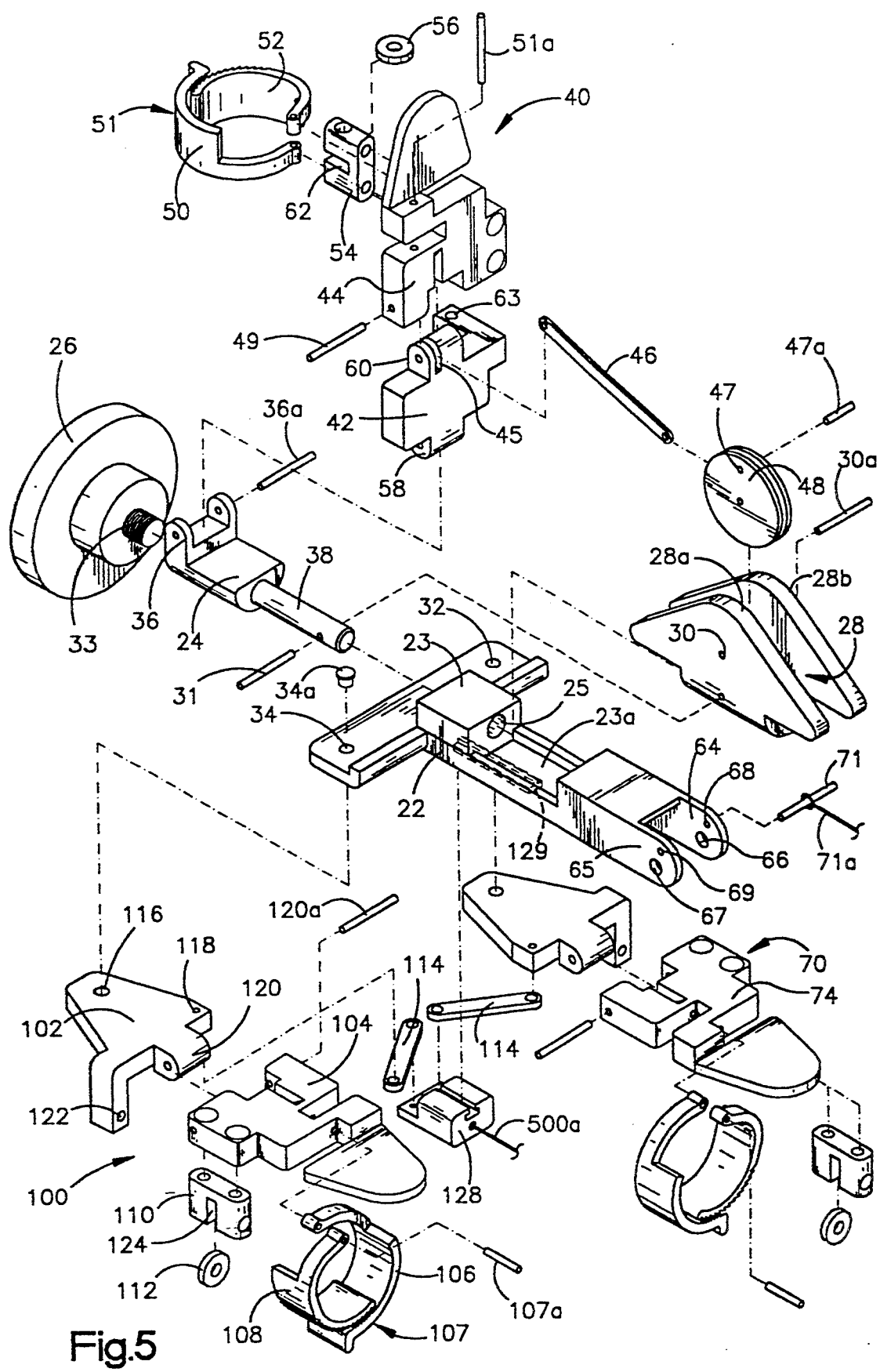
FIG. 5 is an exploded perspective view of the master hand portion of the surgical hand shown in FIG. 1.

As best shown in FIG. 5, the central component of the hand 20 is a handle or base plate 22. The base plate 22 includes mounting locations for mounting the various functional parts of master hand 20.

As shown, the base plate 22 is T-shaped and has a central pivot block mounting base 23 which is generally square in cross section and is oriented along the leg of the "T" in the distal direction from the cross-arm of the "T" in the assembled hand 10. The pivot base 23 has a cylindrical aperture 25.

The mounting base 23 provides a mounting location for a thumb assembly 40. Further distally removed from the intersection, along the central shaft or leg of the "T" is an open portion 23a, which is defined by spaced mounting arms 64 and 65. The open portion 23a receives a U-plate 28. On the underside of the lower face of the base plate 22 is a slide rail 129. Projecting from the distal end of a handle plate support portion 21 are the vertically mounted arms, master support plate left mounting arm 64 and master support plate right mounting arm 65. Each mounting arm has two openings for receiving pivot pins for a cylindrical block or post 230, which is secured by a pivot or cross pin 71.

At the ends of the arms of the "T" are located left and right finger mounting openings 32 and 34 respectively. The openings 32 and 34 are adapted to receive a pivot pin (not shown) for pivotally attaching a left finger assembly 70 and a right finger assembly 100.

Both finger assemblies 70 and 100 are essentially identical, save for their being mirror images of one another. Thus, while both are shown in the drawings, only the right finger assembly 100 will be described in detail, except where necessary to provide details of the interactions of the finger assemblies 70 and 100.

The finger assembly 100 includes a support plate 102 provided with an opening or first pivot point 116. The first pivot point 116 is adapted to be pivotally attached to the pivot pin (not shown) extending through the opening 34 in base plate 20. The finger assembly 100 is thereby given the capability of pivoting towards and away from finger assembly 70 in a single common plane therewith. This motion corresponds with the motions known as adduction and abduction, respectively, of the human fingers. The master finger assemblies 100 and 70 are thus capable of moving with the fingers of the human operator as the human fingers are spread apart from a substantially aligned position to an angularly related, V-shaped position, and moved back towards each other. The support plate 102 corresponds to the first phalange of a human finger.

The support plate 102 includes a hinge portion 120 attached by a hinge pin (not shown) to a corresponding hinge portion on finger plate 104. The interphalangeal joint hinge thus defined corresponds to an interphalangeal joint on a human finger, and allows hinged movement of finger plate 104 relative to support plate 102. Thus, the hinged movement about the interphalangeal joint of finger assembly 100 corresponds to and is actuated by movement of the human operator's finger bending in flexion. When the human finger is extended, finger assembly 100 likewise moves in extension.

The support plate 102 includes a second pivot point or opening 118. The opening 118 is adapted to receive a pivot pin (not shown) by which a first end of a link 114 is attached to support plate 102. The link 114 is attached by its second end to a slide block or slider 128, which is adapted for movement in a proximal-distal direction in response to spreading or returning motion of finger assemblies 100 and 70. The slider 128 is movably attached to a slide rail 129 on the underside of the base plate 22.

When the finger assemblies 100 and 70 are spread, from an aligned position, away from each other, to a V-shaped position, by the analogous action of the attached human hand, the slider 128 is moved in the distal direction, imparting motion to a first motion transmission rod 500 by a flexible cable 500a connecting the block 128 to the distal hand 150, causing corresponding motion in the distal hand. Conversely, when the finger assemblies 100 and 70 are moved back toward each other, the slider 128 is drawn in the proximal direction, which in turn pulls the cable 500a and the first motion transmission rod 500 in the proximal direction, again causing corresponding motion in the distal hand 150. Thus, the linkage between the finger assemblies of the master hand actuates the motion transmission rod and cables, which in turn actuates the linkage between the slave fingers, thereby creating a one-for-one correspondence between the positions of the control and controlled fingers.

In the embodiment thus described, the finger spreading and returning capability creates an equal and opposite motion of finger assemblies 100 and 70. In other words if, for example, right finger assembly 100 spreads outward at an angle of 25°, the mechanism as shown in the drawings operates such that left finger assembly 70 simultaneously spreads 25° outward, in the same plane but in a direction laterally opposite that in which finger assembly 100 moves. While this is the preferred embodiment, other embodiments are possible wherein the finger assemblies are independently spreadable, or in which the simultaneous spreading is not equal in both directions.

The support plate or first phalange 102 further includes a cable slot 122 through which a flexible cable 133 passes. The cable 133 transmits motion from movement of the finger plate or second phalange 104 to the distal hand 150 by means of a second motion transmission rod 510 providing connection therebetween.

The motion transmitting flexible cable 133 includes a stationary sheath (not shown) within which the motion transmitting cable or rod moves. The sheath is attached to the support plate 102 where the cable 133 passes through a support plate cable slot 122. The cable 133 is attached to a cable block 110 mounted on the second phalange 104.

A third motion transmission rod 520, connected to a left master finger flexible cable 136 (FIG. 6), which is attached to the left master finger assembly 70, provides substantially equivalent connection from left master finger assembly 70 to the distal hand 150, as does the second rod described for the right master finger assembly 100.

The finger plate 104, hingedly attached to the support plate 102, corresponds to the second phalange of a human finger. The plate 104 moves about the hinge defined by its attachment to the support plate 102 in a motion corresponding one-for-one to that of a bending human finger, moving in flexion and extension. This bending motion is transmitted by the aforementioned flexible cable 133 as shown in FIG. 1, to distal hand 150. The motion transmitting cable 133 is attached to the finger plate 104 at a cable block 110. The exact operative position of the motion transmitting cable is adjustable by movement of a cable adjusting nut 112, mounted in a finger plate cable slot 124 provided in the block 110.

The finger plate 104 includes a clamp assembly 107 for releasably but firmly attaching the finger of the human operator to the finger plate 104. The clamp assembly 107 shown in FIG. 5 includes a top clamp portion 106 and a bottom clamp portion 108. The upper side of the bottom portion 108 has lateral grooves matching lateral grooves in the lower side of the top clamp 106. The interlocking of these grooves provides the releasable attachment of the corresponding human finger to the finger assembly 100 of the master hand 20. The top clamp portion 106 further comprises an outwardly extending tab for use in releasing the interlock between the top and bottom clamp portions when the clamp is closed.

As previously indicated, the left finger assembly 70 preferably is the mirror image of the right finger assembly 100. Thus, each feature described for the right finger assembly 100 has a corresponding and equivalent feature on the left finger assembly 70. Where preferred, some parts may not be mirror images.

The master hand 20 further includes a centrally mounted, swivelable thumb assembly 40. The thumb assembly 40 includes a thumb block or first phalange 42, which is hingedly mounted by a joint hinge formed by the attachment of a thumb block mounting hinge portion 58 to a pivot block thumb mounting portion 36 on a pivot block 24, by a pivot pin (not shown). The thumb block or first phalange 42 is thereby allowed to hingedly move in a proximal-distal direction, or in other words, towards or away from the finger assemblies 100 and 70 of the hand 20. The thumb first phalange 42 corresponds to a first phalange of a human thumb.

The thumb first phalange 42 includes a second hinge portion or joint hinge 60. The hinge portion 60 corresponds to a thumb interphalangeal joint of a human hand and is hingedly attached to a thumb plate or second phalange 44 by a pivot pin (not shown). The thumb plate 44 thereby corresponds to a second phalange of a human thumb, and is capable of one-for-one corresponding movement with an attached human thumb. Thus, when the human operator's thumb moves in flexion and extension, the thumb assembly 40 of the hand 20 moves in a one-for-one corresponding motion of flexion and extension.

It should be noted that when the term "one-for-one correspondence" is used in reference to the present invention, it does not necessarily mean that the movements of the corresponding elements are exactly of the same magnitude or in exactly the same direction. What "one-for-one correspondence" means is that for each position of a particular element said to be in this relationship, there is one and only one position of the corresponding element in the relationship. Generally, the positions of the elements of the master hand said to have a one-for-one correspondence with positions of the elements of the slave hand will be parallel and of similar purpose, but they may or may not have the same magnitude of motion.

The thumb block interphalangeal hinge portion 60 further includes a slot 45 which pivotally receives a thumb actuator link 46. The link 46 is held in place in the slot 45 by means of a pin 49. This pin 49 may be the same pin used to form the thumb interphalangeal hinge between the first 42 and second 44 thumb phalanges. The link 46 is attached to the thumb first phalange 42, and it is responsive to hinged movement of the phalange 42 as in moves in a motion corresponding to palmar adduction and abduction of the human hand. The link 46 is not actuated by movement of the second phalange 44 in its movement about the interphalangeal hinge relative to the first phalange 42 but is actuated only by movement of the first phalange 42 relative to the pivot block 24.

Thus, the thumb assembly 40 is capable of moving towards the finger assemblies 100 and 70 in a movement analogous to a human thumb moving towards the human fingers of a hand in a motion referred to as palmar adduction, and moving away from the fingers in a movement known as palmar abduction. When the thumb assembly 40 so moves, the motion is transmitted toward the slave hand 150 by the link 46.

The thumb plate 44, hingedly attached to thumb block 42, corresponds to the second phalange of a human thumb, and the joint hinge corresponds to an interphalangeal joint of a human thumb. The plate 44 moves about the hinge defined by its attachment to support plate 42 in a motion parallel to that of a bending human thumb. This bending motion is transmitted by a flexible cable 142 (FIG. 1) to distal hand 150, by means of a fifth motion transmission rod 540 connected to the flexible cable 142. The flexible cable 142 is covered by a sheath (not shown) which passes through and is immobilized by an aperture 63 in the block 42. The motion transmitting flexible cable 142 is attached to the thumb plate 44 at a thumb cable block 54. The exact operative position of the motion transmitting cable is adjustable by movement of a cable adjusting nut 56, mounted in a thumb plate cable slot 62 provided therefor in the block 54.

The thumb plate 44 includes a clamp assembly 51 for releasably but firmly attaching the thumb of the human operator to the plate 44. The clamp assembly 51 includes a top clamp portion 50 and a bottom clamp portion 52. The upper side of the bottom portion 52 has lateral grooves matching the lateral grooves in the lower side of top clamp 50. The interlocking of these grooves provides the releasable attachment of the corresponding human thumb to the thumb assembly 40 of master hand 20. The top clamp portion 50 further comprises an outwardly extending tab for use in releasing the interlock between the top and bottom clamp portions when the clamp is closed.

The thumb assembly 40, as described, is hingedly attached to a pivot block 24. The pivot block 24 includes a pivot block shaft 38, axially extending in the distal direction from the thumb attachment hinge. The shaft 38 extends through the cylindrical aperture 25 in the mounting base 23. The shaft 38 has a diameter which permits it to swivel in the cylindrical aperture 25. When the shaft 38 is fully introduced into the aperture 25, the shaft 38 projects beyond the distal end of the mounting base 23.

The shaft 38 also projects into an aperture 29 provided in a lower section 27 in the U-shaped plate 28 and is pinned thereto by a pin 31. The U-shaped plate 28 holds a thumb roller wheel 48 between spaced upper arms 28a and 28b. The wheel 48 is freely rotatable about an axle 30 fixed to and extending between the arms 28a and 28b.

The lower section 27 of the U-plate 28 is rounded and the entire thumb assembly 40, including the thumb phalanges and attachments thereto, the pivot block on which the thumb phalanges are mounted, and the U-plate assembly are all locked into a unit, and the unit is swivelable left and right, with the shaft 38 constituting the axis of rotation. Thus the thumb assembly 40 is enabled to swivel back and forth laterally. This capability allows the hand 20 to be operated by either the left or right hand of the human operator.

Figure 6:
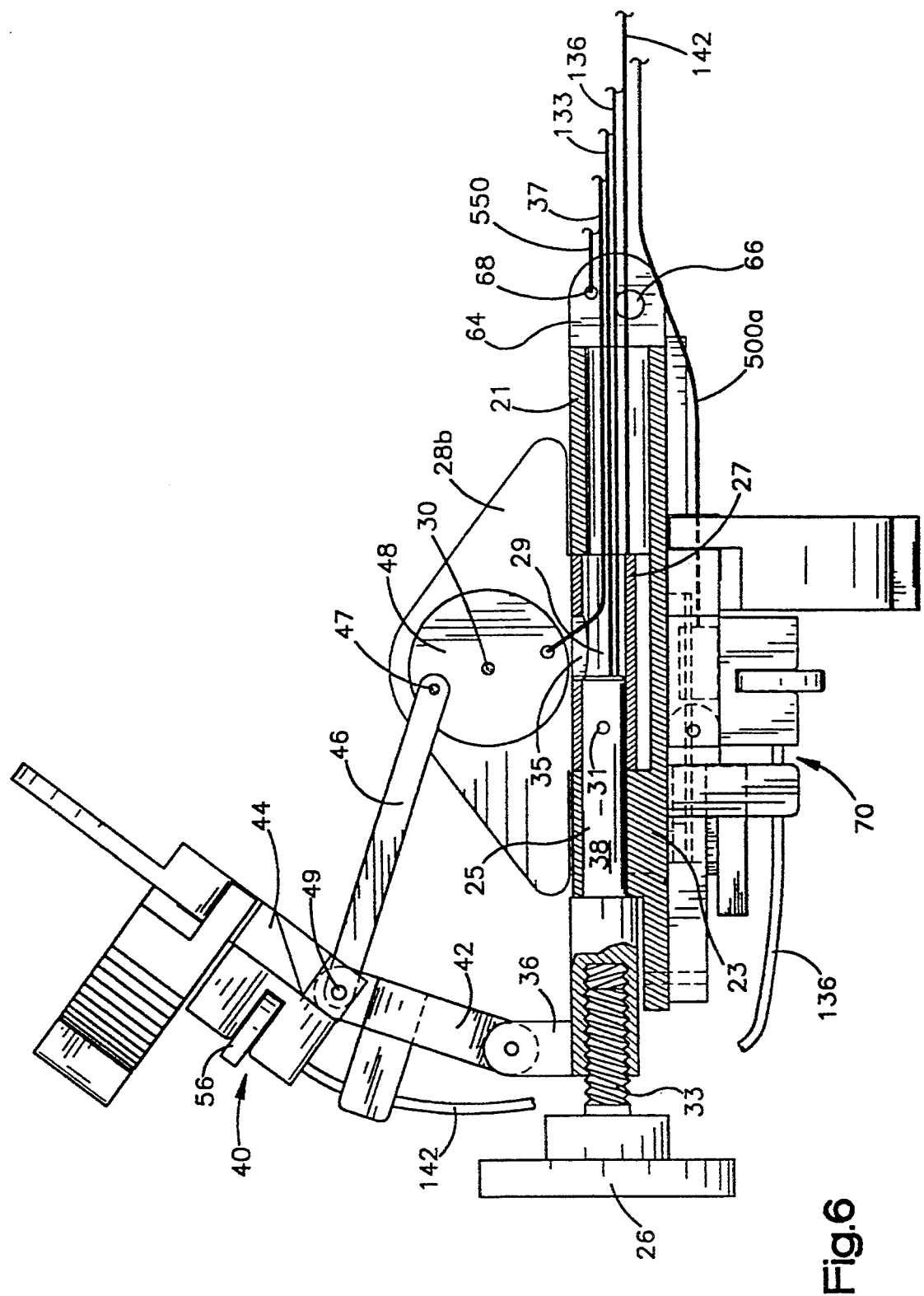
FIG. 6 is a partial sectional view of the master hand portion of the invention.

As best shown in FIG. 6, the U-plate 28 includes an opening 35. The fourth motion transmission rod or cable 37 is attached to the wheel 48 and extends through the opening and towards the shaft 12. The opening 35 allows the flexible cable 37 together with the cables 136 and 142 to pass into the aperture 29 and into the distal portion of handle plate 22, where the flexible cable may be attached to a motion transmission rod. Also it may be noted that the cable 500a passes beneath the plate 22 and toward the shaft 12.

The thumb actuator or link 46 has been described as attached at one end to the thumb block or first phalange 42. The second, distal end of the link 46 is attached at or near the top of the thumb roller wheel 48 at a pivot 47 to an inner portion of the wheel as best shown in FIG. 6. Thus, when the thumb moves in a direction toward the wheel 48, which corresponds to palmar adduction, the wheel 48 is caused to rotate in a clockwise direction as viewed in FIG. 6. The cable 37 is attached at the diametrically opposite side of the wheel 48 from the link attachment point and extends to a fourth motion transmission rod 530. Thus, when the thumb assembly 40 moves in palmar adduction, the top of the wheel moves distally, and the bottom of the wheel, where the cable 37 is attached, moves proximally. The wheel 48 acts to pivotally reverse the motion of the thumb assembly 40 before transferring this motion to the distal thumb via its connection to the fourth rod 530. The cable 37 and the fourth motion transmission rod 530 thereby transmits motion to the distal hand in the reverse direction to the movement of the thumb.

When the thumb first phalange 42 moves away from the fingers, in palmar abduction, the wheel 48 rotates counterclockwise and the fourth rod is pushed distally. Thus, the wheel 48 operates to reverse the direction of motion transmitted from the thumb first phalange 42 moving in either palmar adduction or palmar abduction.

The master hand 20 further includes a palm plate 26, which allows the human operator of the surgical hand 10 to adjust the overall size of the hand 20 in order to fit the varying sizes of various human operators using the surgical hand 10. The palm plate 26 has a threaded shaft 33 which is threaded into the pivot block 24. Thus, by rotating the palm plate in a manner to back the threaded shaft 33 out of the block 24, the master hand 20 is essentially made larger, able to fit a human hand having longer fingers. This feature, in addition to the swivelability of the thumb assembly 40, further increases the usefulness of the manipulable surgical hand 10, since persons having varying handedness and hand size can use the same master hand 20.

Figure 2:
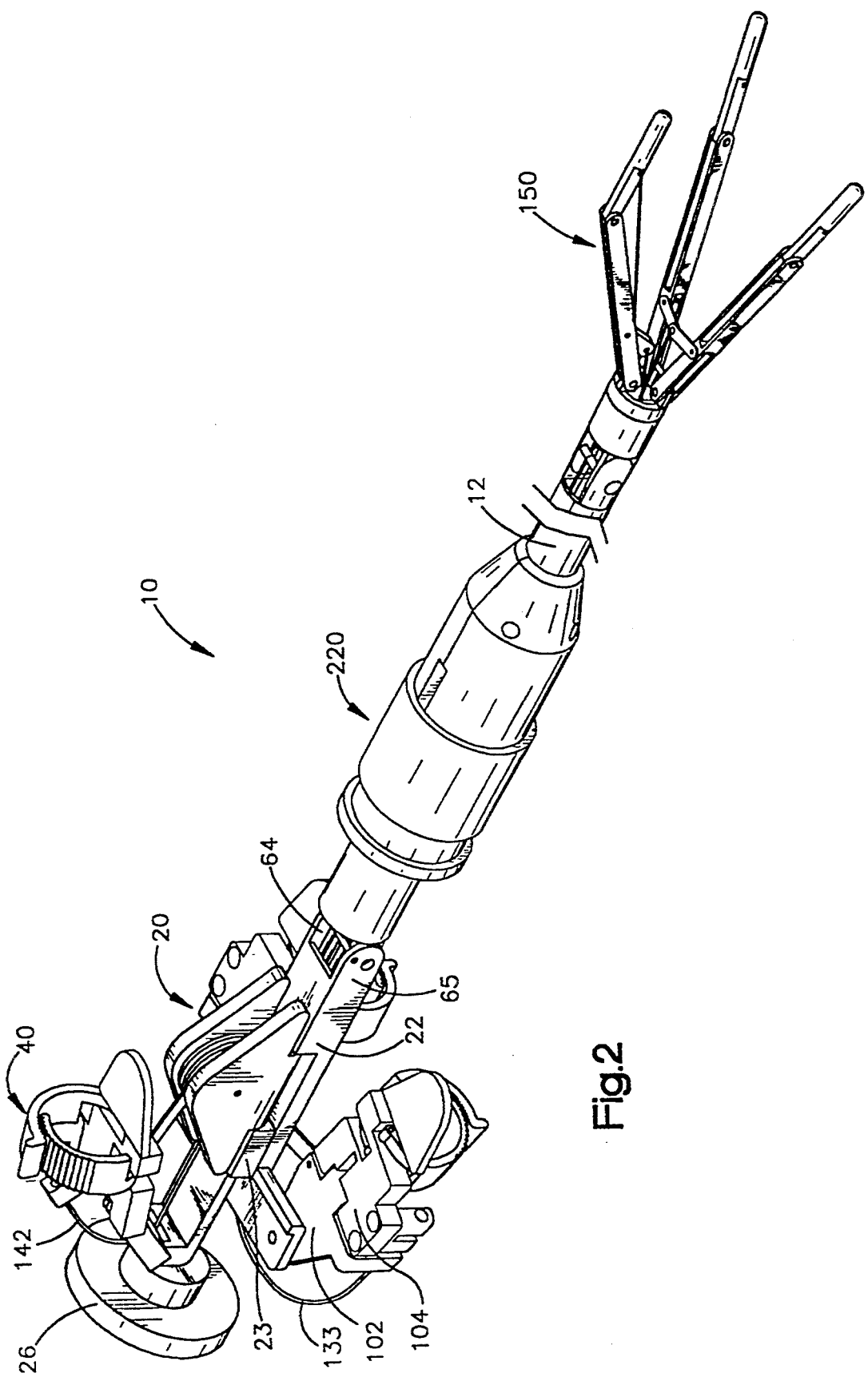
FIG. 2 is a view of the hand shown in FIG. 1 with the fingers and thumb in a manipulated position.
Figure 3:
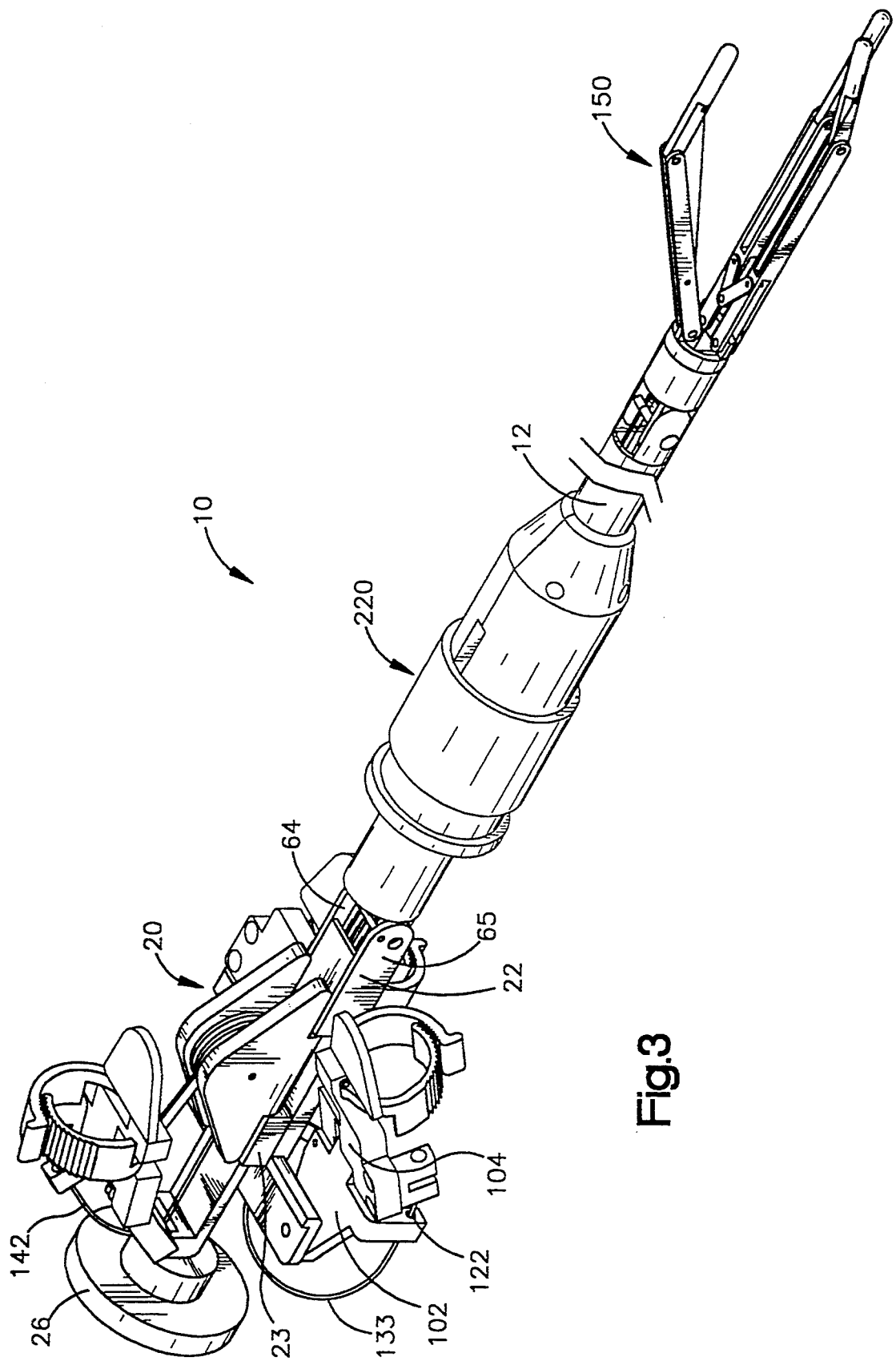
FIG. 3 is a view of the hand shown in FIGS. 1 and 2 with the fingers and thumb in another manipulated position.
Figure 4:
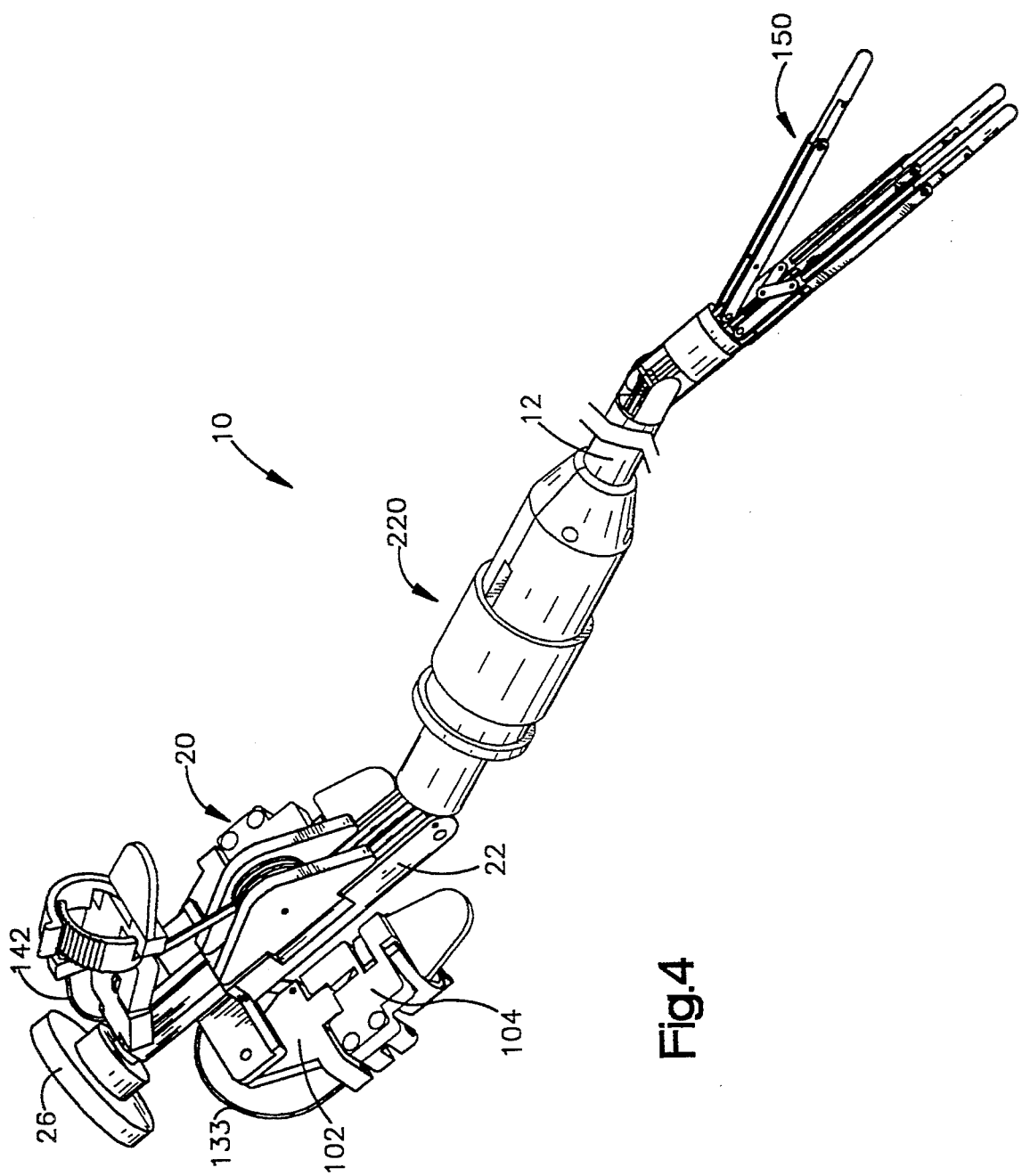
FIG. 4 is a view of the hand shown in FIGS. 1-3, illustrating the wrist in a displaced condition.

As shown in FIGS. 2, 3, and 5, at the distal end of handle plate 22, or at the base of the "T" of the handle plate, are located a pair of arms for mounting the master hand 20 on shaft 12. The left master support plate mounting arm 64 and right master support plate mounting arm 65 extend distally from the base of the "T" of the handle plate 22, and are employed for the purposes of mounting the master hand 20 and the remaining distal portions of the manipulable hand 10, and for forming a master hand wrist. The master hand 20 may move in a vertical plane relative to the shaft 12, to generate a bending motion about the master wrist and to transmit this motion to a distal, slave hand wrist by means of a sixth motion transmitting rod 550.

The left master mounting arm 64 and the right master mounting arm 65 each have two openings which accept pivot members 208 and 212 provided on pivot arms 209 and 213 which extend from a cylindrical block 210. Each mounting arm 64 and 65 also has a cross pin opening 68 and 69 which carry the cross pin 71.

Referring now to FIGS. 5 and 8, the left and right pivot members, 208 and 212, are disposed upon the left and right handle pivot arms 209 and 213, respectively. The members 208 and 212 have a diameter allowing them to snugly but pivotably fit within the left and right pivot pin openings 66 and 67, respectively, disposed on the master mounting arms 64 and 65.

The cross pin 71 extends between and is mounted through the openings 68 and 69. The pin is attached to a short stiffly flexible cable 71a which, in turn, is connected to the sixth motion transmission rod 550, which transmits motion generated by movement of the wrist about the pivot pin to the corresponding distal wrist. The connections provided by the cross pin mountings and the pivot pin mountings, together with the corresponding mountings on the distal wrist, the sixth rod 550, and the hollow tube 12 constitute a parallel linkage capable of generating the wrist-like motion described above.

As may be seen most clearly in FIGS. 8–11, the motion transmitting rods 500 through 550 are reciprocable within passageways in the coupling assembly 220 and the sleeve 12 and terminate at a slave or distal wrist at the distal end of the sleeve 12.

The sixth motion transmission rod 550 connecting the wrists causes the distal wrist to move approximately parallel to movements generated by the master wrist, as actuated by movements of the human operator's hand. The master and distal wrists move in parallel motion due to their attachment to each other by the parallel linkage. As with positions of other corresponding master and slave structures of the manipulable hand 10, the distal wrist position is in one-for-one correspondence with positions of the master wrist.

The following describes the structure and operation of the illustrated embodiment of the distal wrist 560 and the distal hand 150.

Figure 7:
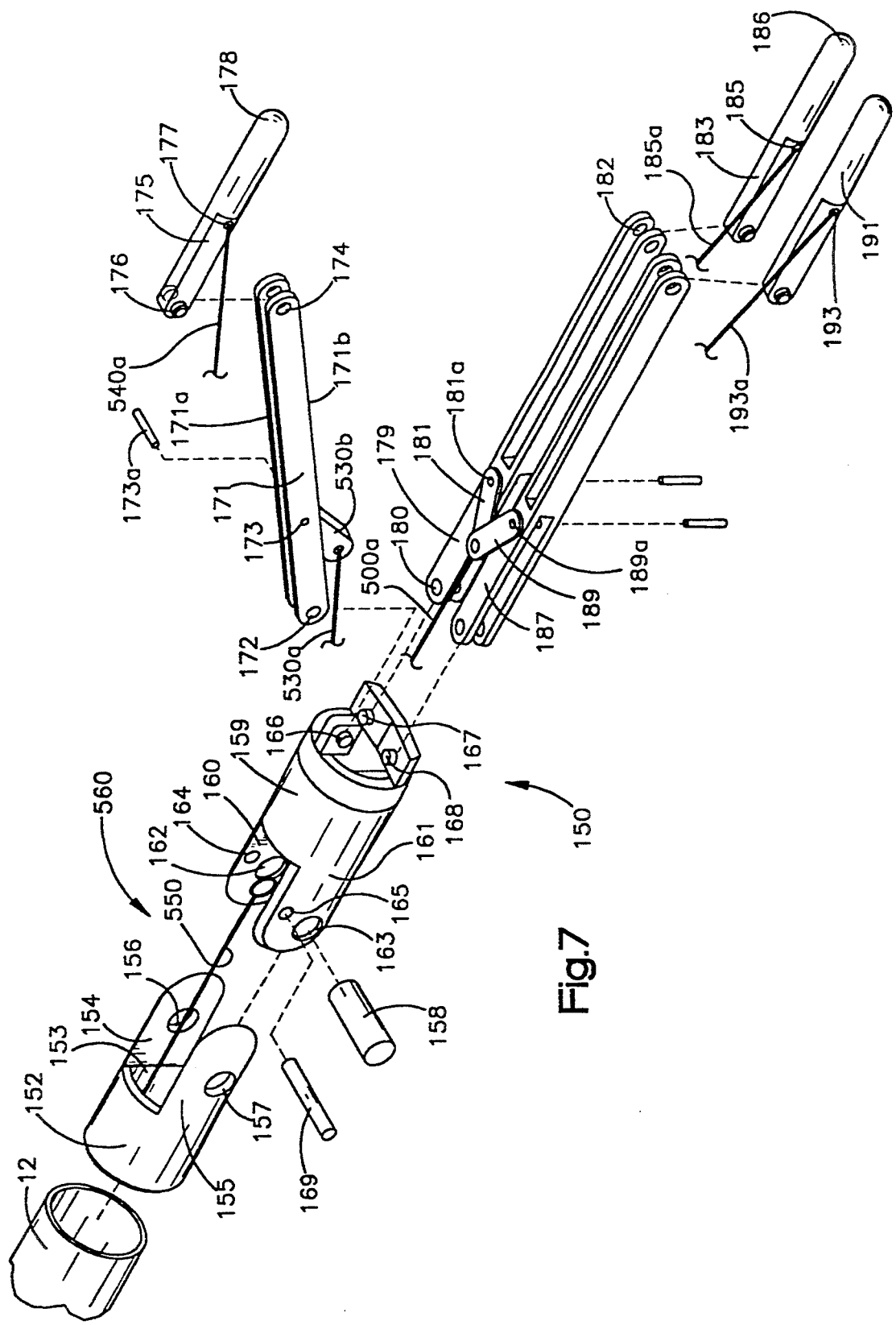
FIG. 7 is an exploded perspective view of the slave hand portion of the invention.

The basic elements of the slave, distal, or control hand 150 are best shown in FIG. 7. The hollow, elongated sleeve 12 has already been described in relation to the master hand 20. The distal end of sleeve 12 is attached to a cylindrical portion of a distal support post 152. Preferably the inner diameter of the cylindrical portion of the post 152 is selected to snugly receive sleeve 12 therein. The post 152 has two arms, a left support arm 154 and a right support arm 155, extending distally from the cylindrical portion on opposite sides of the support post 152. The left and the right arms, 154 and 155, have pivot attachment openings 156 and 157, respectively, for receiving a pivot pin 158 which pivotally attaches the post 152 to a mounting base pivot post 159.

The pivot post 159 has two pivot arms, 160 and 161, pivotally attached to the support post arms 154 and 155. Both pivot arms have openings, a left pivot attachment opening 162, and right pivot attachment opening 163. The pivot arms 160 and 161 fit snugly but pivotably between the support arms 154 and 155, such that openings 156, 162, 163 and 157 are aligned by the pivot pin 158. When the pivot pin 158 aligns these openings, the wrist or pivotable joint for the distal hand 150 is formed. The attachment allows free swiveling movement of the pivot post 159 in a vertical plane relative to the support post 152, thereby allowing the joint to act as a wrist.

The six motion transmission rods 500, 510, 520, 530, 540, and 550 connected to the master hand 20 pass through the coupling assembly 220 and the elongated tube or sleeve 12, and emerge through a central opening 153 of the support post 152. Stiffly flexible cables attached to five of these rods continue into and through the cylindrical portion of the pivot post 159, to control operation of the distal hand 150.

The sixth motion transmission rod 550 passes through the hollow portions of the sleeve 12 and the support post 152, and is pivotally connected to a wrist actuating pin 169 in the distal wrist 560. The wrist actuating pin 169 is attached to and mounted between the openings 164 and 165 in the pivot arms 160 and 161. The pivot actuating openings 164 and 165 are slightly vertically offset from the pivot arm openings 162 and 163, such that motion transmitted to wrist actuating pin 169 causes pivot post 159 to move about the pivot pin 158 which acts as a fulcrum or central pivot point about which the wrist bends.

As may be seen most clearly in FIGS. 8-11, the motion transmitting rods 500 through 550 are reciprocable within passageways in the coupling assembly 220 and the sleeve 12 and terminate at or near the distal end of the sleeve 12.

The distal end of the pivot post 159 comprises mounting positions for each of the digits of the slave or controlled hand 150. As shown in FIG. 7, in the preferred embodiment mountings are provided for three digits, a thumb and two fingers. A thumb mounting stud 166 is preferably adapted to provide horizontally oriented posts allowing vertical pivoting of the slave thumb about the pivot point created by the mounting 166. These thumb movements correspond to palmar adduction and abduction in master hand 20 and in the human operator's hand.

Two finger mounting studs 167 and 168 are vertically oriented posts allowing the slave fingers to pivot in a horizontal plane. This horizontal movement corresponds to the spreading movement of the human operator's hand and the master hand 20 discussed above. Spreading movement of master fingers has been described above. When the slider block 128 moves distally, the first motion transmission rod 500 is pushed distally via its connection to the block 128. At the distal end of a stiffly flexible cable 500a connected to the end of the first motion transmission rod 500, are spreader links 181 and 189, pivotally connected to each other and to the slave fingers. The attachment to each finger is made at left and right spreader link attachment points, 181a and 189a, respectively, on a first phalange 179 and 187 of each slave finger.

The finger portions which comprise the phalanges 179 and 187 are directly attached to the finger mountings 167 and 168 and correspond to the first phalange of the master hand 20, and are referred to as a distal left finger first phalange 179 and a distal right finger first phalange 187. Each first phalange has attached to it a second phalange, 183 and 191. The point of attachment is preferably an interphalangeal joint hinge. The interphalangeal joint hinge at which the first and second phalanges are attached to one another corresponds to an interphalangeal joint in the master finger, which in turn corresponds to an interphalangeal joint in a human finger. In operation, these correspondences are one-for-one.

Each second phalange 183 and 191 is actuated by motion transmission cables 193a and 185a which extend from cable mounts 193 and 185, respectively, on the second phalanges 191 and 183 to the end of the second and third rods 510 and 520, respectively. The interconnection provides one-for-one correspondence of positions between each of the master and slave second phalanges, as this term has been defined above. Thus, the slave fingers are capable of moving in flexion and extension in one-for-one correspondence with the master hand fingers, as the latter are manipulated by the hand of a human operator. Each second phalange of the master hand is linked to the corresponding second phalange of the slave hand by flexible cables and motion transmission rods. The rod portions are defined as the second 510 (right second phalange) and the third 520 (left second phalange) motion transmission rods. Each end of the motion transmission rod is connected to its corresponding second phalange by stiffly flexible cables, which, along with the motion transmission rods, constitute motion transmission means.

The left and right slave fingers are identical to each other in the preferred embodiment depicted in FIG. 7, and so only the left slave finger will be fully described, except to the extent necessary to describe the interactions of the left and right distal fingers.

The left first phalange 179 preferably provides channels wherein motion transmission cables and rods may be retained out of the way and in a position to provide the maximum level of control to the user of the manipulable hand 10. Thus, the first phalanges 179 and 187 may be tubular or channeled. As shown in FIG. 7, the preferred form is a member having two channeled segments, one oriented horizontally and one vertically.

The horizontally oriented channel segment is more proximal, and allows for the horizontal mounting of the finger, and the aforementioned movement in a horizontal plane. Furthermore, the horizontal channel allows a laterally oriented connection between the first motion transmitting rod and each finger, in which this motion transmission rod is centrally disposed between the fingers and capable of causing them to spread outwardly in the same plane.

The channel may be obtained by using an I-beam having a partly or mostly open web, particularly toward the attachment end, or by using U-shaped channel stock with the "base" of the "U" being partly or mostly open, particularly toward the attachment end. The spreader links 181 and 189 are located along this segment of the channel. The distance from the base mount 180 may be varied in regard to various parameters, such as the maximum spreading angle between the fingers, the ratio of distally linear movement of the first motion transmission rod to the angle or distance between the spread fingers, and the length of the motion transmission rod or other means exposed during spreading, i.e., exposure possibly causing interference by the cable or rod with operative functions of distal hand 150.

If tubular stock is used, suitable openings for motion transmission means and openings or posts for attachment should be provided at each end of the tube.

The vertically oriented channel segment is more distal, and preferably provides a channel for the flexible cables used to actuate movement of the second phalange attached to each first phalange. This segment may be made from material either the same or different, tubular or channeled, as the horizontal segment. At the distal end of this segment are openings, or second phalange mounts 182 for mounting the second phalange 183 to the first phalange 179. As depicted in FIG. 7, the second phalange is thereby allowed to move in a vertical plane, coplanar with the first phalange.

The relative length of the horizontally and vertically oriented segments of first phalange 179 is variable within a wide range. The only restriction being that the first phalange 179 should be freely horizontally movable by operation of the spreading links attaching this phalange to the first motion transmission rod, and the second phalange should be freely movable through its designed range of motion in response to its motion transmission rod.

The second phalange 183 has a mounting post 184 on its proximal end, which fits into the openings 182 on the first phalange 179. The second phalange 183 may preferably be made from round stock, with a flattened segment extending part of the length of the second phalange. The flattened segment will preferably extend from the distal end of the second phalange at least to the vicinity of the flexion cable mount opening 185. A tip 186 of the second phalange 183 is preferably cylindrical, with a rounded distal end. The tip 186 may be made of the same or different material as the remainder of the second phalange 183, which in turn may be the made from the same or different material as that of the distal hand 150 generally. If the tip 186 is of a different material, it may be any material consistent with use in laparoscopic surgery. If it is a separately attached piece, it may be snapped on, threaded on, or applied in a thin layer as a coating. If the tip 186 is a separate material, it is preferably easily removable and disposable.

The second phalange 183 is actuated and controlled by the flexible cable 185a connected to the distal end of the third motion transmission rod 520, which is in turn actuated and controlled by action of the left second phalange or master plate 74 of master hand 20. As with the other portions of distal hand 150, the movement and positions of the second phalange 183 is in one-for-one correspondence with that of the plate 74, as the term "one-for-one correspondence" has been defined hereinabove.

The second phalange 191 of the right slave finger is actuated and controlled by the flexible cable 193a connected to the distal end of the second motion transmission rod 510, which is in turn actuated and controlled by action of the right second phalange or finger plate 104 of master hand 20. As with the other portions of distal hand 150, the movement of right second phalange 191 is in one-for-one correspondence with that of master second phalange or finger plate 104, as the term "one-for-one correspondence" has been defined hereinabove.

The distal fingers spread in response to movement of the first motion transmission rod 500 and the cable 500a. When this movement is toward the distal hand 150, the distal fingers are caused to spread away from each other, and the fingers move back toward each other when the first rod 500 is drawn back toward the master hand 20. Movement of the first rod 500 is generated by spreading movement of the master fingers 70 and 100 as described hereinabove.

The construction of the parts of the distal hand providing finger spreading is as follows. The first motion transmission rod terminates in the vicinity of the first segment of the first phalange of the finger. Connecting from the terminus of the first rod to the mounting points or mounts 181a and 189a are the two links 181 and 189. These two links 181 and 189 are movably connected at both ends, to provide swiveling in response to movement of the first rod 500. When the first rod 500 and its attached cable 500a move distally, each link is caused to move distally. Since the distal end is attached to the fingers, this end cannot move distally, but instead moves outward, causing the finger to swivel outwardly. Conversely, when the first rod 500 and its attached cable 500a move proximally, the links are drawn proximally, causing the fingers to swivel back together.

The thumb portion of distal or slave hand 150 is mounted on a slave thumb pivot base posts 166. The slave thumb includes a first phalange 171 and a second phalange 175 pivotably mounted on the first phalange 171. The thumb second phalange 175 is substantially similar to and operates according to the same principles as does the slave finger second phalanges 183 and 191.

The thumb first phalange 171, as shown in FIG. 7, is a pair of parallel, flat links 171a and 171b.

The thumb base mount openings 172 are provided in each link 171a and 171b, to mount the first phalange 171 on the thumb pivot base posts 166 of the pivot post 159. This mounting provides for movement of the slave thumb in a vertically oriented plane. Relative to the slave fingers, this movement is equivalent to palmar adduction and abduction, wherein the thumb as a unit moves toward or away from the fingers of the human hand.

An adduction cable mount 173 provides an attachment point for a stiffly flexible cable 530a fixed to the end of the fourth motion transmission rod 530. Actuation by the cable 530a and its rod 530 causes the thumb first phalange 171 to pivot about its attachment at the base mount openings 172, thus causing the slave thumb's movements corresponding to palmar adduction and abduction. The motion transmitting rod 530 is actuated and controlled by movement of the master thumb assembly 40, as the master thumb assembly 40 is controlled by the human operator of the manipulable hand 10. As with other parts of slave hand 150, the adduction and abduction movements of the slave thumb are in one-for-one correspondence, as defined, with similar movements of master thumb 40.

The slave thumb first phalange 171 is further provided with a second phalange mount or opening 174 in each link 171a and 171b for a pair of mounting posts 176 of the second phalange 175. The point of attachment is preferably an interphalangeal joint hinge. The interphalangeal joint hinge at which the first and second phalanges are attached to one another corresponds to an interphalangeal joint in the master thumb, which in turn corresponds to an interphalangeal joint in a human thumb. In operation, these correspondences are one-for-one.

The second phalange 175 may be made from round stock, with a flattened segment extending part of the length of the second phalange, preferably at least to the vicinity of a flexion cable mount opening 177. The tip 178 of the second phalange 175 is preferably cylindrical, with a rounded distal end. The tip 178 may be made of the same or different material as the remainder of the second phalange 175, which in turn may be formed of material the same as or different from that of the distal hand 150 generally. If the tip 178 is of a different material, it may be any material consistent with use in laparoscopic surgery. If it is a separately attached piece, it may be snapped on, threaded on, applied in a layer as a coating, or otherwise attached. If the tip 178 is a separate material, the tip is preferably easily removable and disposable.

The second slave thumb phalange 175 is actuated and controlled by a stiffly flexible cable 540a connected to the distal end of the fifth motion transmission rod 540, which is in turn actuated and controlled by action of the thumb plate or second phalange 44 of master hand 20. As with the other portions of distal hand 150, the movement of the slave thumb second phalange 175 is in one-for-one correspondence with that of the master thumb assembly second phalange or thumb plate 44, as the term "one-for-one correspondence" has been defined hereinabove.

Each of the above described elements of the slave hand is independently responsive to movements of the particular motion transmission rod, and associated flexible cables, with which that element has been described. Thus, each of these six motion transmission rods, operating the fingers, the thumb or the wrist, is separately operable as a result of motions of the master hand as controlled and actuated by the human operator's hand. Each of the elements of the slave hand is movably responsive in one-for-one correspondence with the movements of the master hand.

To summarize, the six motion transmission means comprising the rods and cables perform the following functions. The first rod 500 and its cable 500a connect and provide spreading movement to the fingers, via the slider block 128. The second rod 510 and its cable 510a connect the left master finger second phalange to the left slave finger second phalange. The third rod 520 and its cable 520a connect the right master finger second phalanges to the right slave finger second phalange. The fourth rod 530 and its cable 530a provide the manipulable hand 10 with the capability of palmar adduction and abduction, by connecting the first phalange of the master thumb assembly to the first phalange of the slave hand, via the wheel 48. The fifth rod 540 and its cable 540a connect the master thumb second phalange to the slave thumb second phalange. The sixth rod 550 and its cable 550a provide articulation of the wrists, by providing actuating connection between the master wrist and the slave wrist. Thus, the second, third, and fifth rods provide the fingers and thumb of hand 10 with the capability of moving in flexion and extension.

The quick-connect coupling assembly 220 provides for radial alignment of each of the six motion transmission rods or cables, for controllable disconnection of the rods, and for reproducible reconnection of the correct rods. In other embodiments, the coupling may also provide adaptable connection to other embodiments of the distal hand, i.e., having fewer or different functions controlled by the six motion transmission rods, or by having additional rods for additional functions, such as third phalanges.

As best shown in FIGS. 8–11 and FIGS. 12–25, the coupling assembly 220 includes a top cover 224, a bottom cover 225, and the cylindrical block or handle pivot post 230.

The pivot post or cylindrical block 230 includes a body portion provided with a circular array of axial bores 232. Each bore 232 receives one of the rods 500-550 (FIG. 10a) and terminates at a cup-shaped open end 234. The cup-shaped open end 234 is formed by arcuate wall portions 233. The cup-shaped end 234 has an outside cylindrical surface 231 and a radially extending locking lip or detent tab 236 and is provided with a plurality of axially extending slits 238 which permit the lip or tab 236 to be flexed radially inwardly.

The post 230 is adapted to be connected to a coupling casing or hollow cylindrical sleeve 240 which includes the cooperating coupling halves 224 and 225. The coupling casing or hollow cylindrical sleeve 240 has an axial bore forming a cylindrical sleeve 246 which slidably carries a spring biased locking sleeve 248 which is biased towards the post 230 by a spring 250. The locking sleeve 248 has an outside surface having a diameter adapted to fit within the inside diameter of the cup-shaped end 234 of the cylindrical block 230.

A counterbore 252 forms an open mouth 254 which is adapted to receive and surround the cup-shaped end 234 upon connection of the post 230 and the casing 240. The counterbore is provided with diametrically opposed guide slits 256 and 258 which extend from the open mouth 254 to an annular locking groove or pocket 260 and which receive the lips or tabs 236. The outside diameter of the lips is slightly larger than the inside diameter of the cylindrical wall formed by the slots 256 and 258 so that the lips 236 and 238 are forced radially inwardly as the cup-shaped end 234 is inserted within the open mouth 254. Moreover, it should be noted that the slots 256 and 258 keep the mating members comprising the post 230 and the casing 240 in proper mating alignment.

Each rod 500-550 comprises a mating pair of rods that includes a male mating end 262 and a female mating end 264. Each male mating end has a bullet-nosed tip 268 which is adapted to be received in a split socket 270 provided at the end of each mating end 264. Each female end 264 is square in cross section and is slidably carried in its own one of a radial array of longitudinally extending peripheral slots 272 provided in a carrier guide core or cylindrical plug 274. The number of the peripheral slots 272 is equal to the number of the axial bores 232. An end of the carrier guide core or plug 274 is closely surrounded by the inside surface of locking sleeve 248 which is slidably mounted on the core 274. The core 274 is adapted to guide the motion transmission cables or rods for axial movement through the coupling assembly 220, by its axially extending peripheral slots 272. Each motion transmission rod or cable is held within its own axially extending peripheral slot 272 in carrier guide core 274. The guide core 274 further acts to maintain the rods in their correct relative positions during coupling and uncoupling operations.

To connect or disconnect the coupling members, all of the fingers and the thumb are extended to a straight, axially aligned position and the wrist is placed in an unflexed position. Preferably, this is the position from which the distal hand is inserted into the cannula used for laparoscopic surgery. In this position all of the ends of the male and female mating ends are coplanar as illustrated in the drawings. It may be noted that the tips 268 are spaced from a bottom wall 276 of the cup-shaped end 234 while the sockets 270 are spaced from an end 278 of the guide core 274 but are surrounded by the locking sleeve 248. The distal portion of the assembly is positioned so that the position of the thumb corresponds to the position of the master hand.

When the lips or tabs 236 enter the slots 256 and 258 each rod 500-550 is properly aligned for connection. As the lips 236 travel along the slots 256 and 258 the lips are biased or forced radially inwardly by a cammed surface, and the cup-shaped end 234 engages the end of the locking sleeve 248 as shown in FIG. 9.

The locking sleeve 248 is normally biased to the position illustrated in FIG. 8. In that biased position diametrically opposed wings 280 on the sleeve 248 are resting against one end of a longitudinal slot 282 formed by the casing halves 244 and 245. Interference between the cup-shaped end 234 and the locking sleeve 248 pushes the sleeve 248 against the bias of the spring 250 to expose the sockets 270 of the female ends 264. Alternatively, the sleeve 248 may be withdrawn to its FIG. 9 position against the bias of spring 250 and then cup-shaped end 234 can be inserted. As may be seen in FIG. 9, the bullet-nosed tips 268 enter the sockets 270 and the sockets are permitted to flex open as shown when the sleeve 248 is withdrawn, since the sockets 270 are no longer surrounded by the sleeve 248. When the rod ends are fully inserted and connected in this manner, the lips 236 have entered the locking recess or pocket 260 and sprung back to their non-flexed position, thus permitting the sleeve 248 to be driven back to its position surrounding the sockets 270 by the spring 250 (FIG. 11). In that position the sockets are securely covered by the sleeve 248 to prevent inadvertent separation of the mating halves.

In order to disconnect the assembly, an outer sleeve 290 is provided which is attached to the wings 280. By manually moving the outer sleeve 290 toward the slave hand, the sleeve is shifted so that it no longer surrounds the sockets 270. Thus the radially extending locking lip or detent tab 236 is released from the locking groove 260. As the locking groove 260 and the sockets 270 are now enabled to release the locking lip or tabs 236 and the bullet-nosed tips 268, respectively, axial force permits the tips to be released and disconnected from the sockets.

Although a manipulable hand according to this invention has been illustrated and described in detail, it will be understood that the invention is not limited correspondingly in scope, but includes all changes and modifications coming within the terms of the claims.

What is claimed is:

1. A manipulable surgical hand for performing laparoscopic surgical techniques comprising at least one master control finger, means for releasably attaching said master control finger to a finger of a human hand, said master control finger having at least one interphalangeal joint hinge dividing said control finger into first and second phalanges, all of which correspond to an interphalangeal joint and phalanges of a human hand, said control finger being articulable between extended and flexed positions corresponding to extended and flexed positions of a human finger, an elongated tube having base means for mounting said master control finger at a proximal end thereof, at least one controlled slave finger mounted on finger mounting means mounted on a distal end of said tube, said tube having means for mounting said controlled slave finger at the distal end thereof, said controlled slave finger having at least one interphalangeal joint hinge dividing said slave finger into first and second phalanges, said slave finger being articulable between extended and flexed positions corresponding to the extended and flexed positions of said control finger, motion transmission means carried by said tube connecting said master control finger to said controlled slave finger and being responsive to movement of the phalanges of the control finger to independently transmit movements of each of the phalanges of the control finger to each of the phalanges of the controlled finger with a one-for-one correspondence of movements between the control finger phalanges and the controlled finger phalanges.

2. A manipulable surgical hand for performing laparoscopic surgical techniques comprising at least one master control finger, means for releasably attaching said master control finger of a human hand, said master control finger having at least one interphalangeal joint hinge dividing said control finger into first and second phalanges, all of which correspond to an interphalangeal joint and phalanges of a human hand, said control finger being articulable between extended and flexed positions corresponding to extended and flexed positions of a human finger, an elongated tube having base means for mounting said master control finger at a proximal end thereof, at least one controlled slave finger mounted on finger mounting means mounted on a distal end of said tube, said tube having means for mounting said controlled slave finger at the distal end thereof, said controlled slave finger having at least one interphalangeal joint hinge dividing said slave finger into first and second phalanges, said slave finger being articulable between extended and flexed positions corresponding to the extended and flexed positions of said control finger, motion transmission means carried by said tube connecting said master control finger to said controlled slave finger and being responsive to movement of the phalanges of the control finger to independently transmit movements of each of the phalanges of the control finger with a one-for-one correspondence of movements between the control finger phalanges and the controlled finger phalanges wherein two master control fingers and two controlled slave fingers are provided and wherein each control finger is separately connected to its own one of said controlled slave fingers by said motion transmission means.

3. A manipulable surgical hand according to claim 2 wherein said control fingers are spreadable between a first substantially aligned position and a second, angularly related, V-shaped position, linkage means connecting said control fingers for planar movement between said first and second positions, wherein said controlled slave fingers are spreadable between a corresponding first substantially aligned position and a corresponding second angularly related V-shaped position, said motion transmitting means including means responsive to movement of said control fingers between said first aligned position and said second V-shaped position to move said controlled slave fingers between said corresponding first aligned position and said second angularly related position.

4. A manipulable surgical hand according to claim 3 wherein said linkage means provides a one-for-one correspondence between the positions of said control fingers.

5. A manipulable surgical hand according to claim 4 wherein said means responsive to movement of said control fingers provides a one-for-one correspondence between the position of said controlled slave fingers.

6. A manipulable surgical hand according to claim 4 wherein each said control finger is pivotally connected at a first pivot point to a base plate by a pivot pin, a pair of links pivotally connected to each control finger at second pivot points spaced from said first pivot points, said links being further pivotally connected to a slide block slidably mounted on said base plate for rectilinear motion toward and away from said distal end of said tube, said means responsive to movement of said control fingers including said slide block.

7. A manipulable surgical hand according to claim 6 wherein said means responsive to movement of said control fingers further includes first rod means connected to said slide block and extending through said tube to said distal end adjacent said finger mounting means, each said controlled slave finger being pivotally connected to said finger mounting means, flexible connecting means extending from said first rod means to each said controlled slave finger.

8. A manipulable surgical hand according to claim 1 including flexible cable means fixed at one end to the second phalange of a control finger and fixed at another end to a proximal end of second rod means, said second rod means extending through said tube to said distal end adjacent said finger mounting means, guide means for said cable means adapted to guide said cable for axial movement and to thereby cause axial reciprocation of said second rod means upon articulation of said control finger between extended and flexed positions, flexible cable means extending from a distal end of said second rod means and to the second phalange of said slave finger, whereby axial reciprocation of said second rod means causes articulation of said slave finger between extended and flexed positions with said one-for-one correspondence of movements.

9. A manipulable surgical hand for performing laparoscopic surgical techniques comprising at least one master control finger, means for releasably attaching said master control finger of a human hand, said master control finger having at least one interphalangeal joint hinge dividing said control finger into first and second phalanges, all of which correspond to an interphalangeal joint and phalanges of a human hand, said control finger being articulable between extended and flexed positions corresponding to extended and flexed positions of a human finger, an elongated tube having base means for mounting said master control finger at a proximal end thereof, at least one controlled slave finger mounted on finger mounting means mounted on a distal end of said tube, said tube having means for mounting said controlled slave finger at the distal end thereof, said controlled slave finger having at least one interphalangeal joint hinge dividing said slave finger into first and second phalanges, said slave finger being articulable between extended and flexed positions corresponding to the extended and flexed positions of said control finger, motion transmission means carried by said tube connecting said master control finger to said controlled slave finger and being responsive to movement of the phalanges of the control finger to independently transmit movements of each of the phalanges of the control finger with a one-for-one correspondence of movements between the control finger phalanges and the controlled finger phalanges wherein two master control fingers and two controlled slave fingers are provided, a pair of flexible cables, each of said cables being fixed at one end to the second phalange of a control finger and fixed at another end to a proximal end of second and third rod means, said second and third rod means extending through said tube to said distal end adjacent said finger mounting means, guide means for each of said cables adapted to guide each cable for axial movement and to thereby cause independent axial reciprocation of said second and third rod means upon articulation of said control fingers between extended and flexed positions, flexible cable means extending from the distal end of each of said second and third rod means to the second phalange of a pair of controlled slave fingers, whereby independent axial reciprocation of said second and third rod means causes independent articulation of said slave fingers between extended and flexed positions with said one-for-one correspondence of movements.

10. A manipulable surgical hand for performing laparoscopic surgical techniques comprising at least one master control finger, means for releasably attaching said master control finger of a human hand, said master control finger having at least one interphalangeal joint hinge dividing said control finger into first and second phalanges, all of which correspond to an interphalangeal joint and phalanges of a human hand, said control finger being articulable between extended and flexed positions corresponding to extended and flexed positions of a human finger, an elongated tube having base means for mounting said master control finger at a proximal end thereof, at least one controlled slave finger mounted on finger mounting means mounted on a distal end of said tube, said tube having means for mounting said controlled slave finger at the distal end thereof, said controlled slave finger having at least one interphalangeal joint hinge dividing said slave finger into first and second phalanges, said slave finger being articulable between extended and flexed positions corresponding to the extended and flexed positions of said control finger, motion transmission means carried by said tube connecting said master control finger to said controlled slave finger and being responsive to movement of the phalanges of the control finger to independently transmit movements of each of the phalanges of the control finger with a one-for-one correspondence of movements between the control finger phalanges and the controlled finger phalanges including a master control thumb, means for releasably attaching said master control thumb to a thumb of a human hand, said master control thumb having a joint hinge connecting said master control thumb to a mounting plate, said control thumb being articulable toward and away from said master control finger corresponding to the palmar adduction and palmar abduction of a human hand, means for mounting said master control thumb at said proximal end of said tube, a controlled slave thumb mounted on said mounting means at said distal end of said tube, said controlled slave thumb having a joint hinge, said slave thumb being articulable about slave thumb pivot means toward and away from said controlled slave finger corresponding to the palmar adduction and palmar abduction of a human hand, said motion transmission means including fourth rod means extending through said rod and connecting said master control thumb to the controlled slave thumb with a one-for-one correspondence of movements between the control thumb and the controlled thumb.

11. A manipulative surgical hand according to claim 1 wherein said tube includes coupling means permitting a portion of said tube having said base means to be connected to and disconnected from a portion of said tube having said finger mounting means mounted thereon.

12. A manipulable surgical hand according to claim 11 wherein said coupling means includes means to connect and disconnect a portion of said motion transmitting means connected to said master control finger from a portion of said motion transmitting means connected to said controlled slave finger.

13. A manipulative surgical hand according to claim 12 wherein said coupling means includes releasable locking means.

14. A manipulable surgical hand according to claim 12 wherein said motion transmission means includes rod means extending through said tube, said coupling means comprising a hollow cylindrical sleeve mounted fixed to one end of said portions of said tube, another one of said portions of said tube having a cylindrical block thereon, said cylindrical block having a cup-shaped open end having an outside cylindrical surface adapted to slidably fit within said cylindrical sleeve, arcuate wall portions of said cup-shaped open end having radially extending detent tabs formed thereon, said detent tabs including cam means to bias said tabs radially inwardly to clear an inside surface of said cylindrical sleeve, a locking sleeve slidably mounted within said cylindrical sleeve and having an outside diameter adapted to be received within said cup-shaped open end and adapted to interfere with said radially inwardly biased tabs, pocket means in the inside surface of said sleeve adapted to receive said detent tabs, said rod means comprising a first rod portion slidably extending through an aperture in said cylindrical block, said first rod portion having a bullet-shaped end portion extending into said cup-shaped open end, said rod means further comprising a second rod portion mounted in a cylindrical plug said cylindrical plug being mounted within and fixed with respect to said cylindrical sleeve and having an axially extending peripheral slot slidably mounting said second rod portion, said second rod portion having a socket at its end adapted to radially expand out of said slot to receive said bullet shaped end portion, a spring biased sleeve having an inside surface surrounding said cylindrical plug to prevent radial expansion of said socket, said spring biased sleeve having an outside surface adapted to be received in said cup-shaped open end, and means biasing said sleeve toward said cup-shaped open end.

15. In a surgical instrument for performing laparoscopic surgical techniques through a cannula defined port in a patient, said surgical instrument having a tube adapted to pass through said cannula for access to a surgical procedure site, said tube having manually controlled means at one end thereof adapted to be controlled by a human operator and having a controlled device at another end adapted to perform a surgical technique at said site, in combination therewith the improvement comprising a quick disconnect coupling carried by and dividing said tube into first and second portions to permit separation of said manually controlled means from said controlled device to thereby permit said manually controlled means to be employed with a variety of controlled devices.

16. A surgical instrument according to claim 15 wherein said controlled device is responsive to motion transmission means passing through said tube and connected to said manually controlled means.

17. A surgical instrument according to claim 16 wherein said motion transmission means includes rod means mounted in said tube.

18. A surgical instrument according to claim 17 wherein said coupling means comprises a hollow cylindrical sleeve fixed to said second portion of said sleeve, said first portion of said tube having a cylindrical block thereon, said cylindrical block having a cup-shaped open end having an outside cylindrical surface received within an inside surface of said cylindrical sleeve, arcuate wall portions of said cup-shaped open end having radially extending detent tabs formed thereon, said detent tabs being releasably locked in an annular recess in said inside surface of said cylindrical sleeve, a locking sleeve slidably mounted within said cylindrical sleeve and having a first cylindrical portion extending into said cup-shaped open end and a second cylindrical portion slidably engaging the inside surface of said cylindrical sleeve, spring means biasing said locking sleeve toward said cylindrical block, said rod means comprising a first rod portion slidably extending through an aperture in said cylindrical block, said first rod portion having a bullet-shaped end portion extending into said cup-shaped open end, said rod means further comprising a second rod portion mounted in a cylindrical plug, said cylindrical plug being mounted within and fixed with respect to said cylindrical sleeve and having an axially extending peripheral slot slidably mounting said second rod portion, said second rod portion having a socket at its end receiving said bullet-shaped end portion and adapted to expand out of said slot upon connection to and disconnection from said bullet-shaped end portion, an inside cylindrical surface of said locking sleeve closely surrounding said socket at its end to prevent such expansion and to lock said rod portions in a connected condition.

19. A surgical instrument according to claim 18 wherein said motion transmission means includes a plurality of rods.

20. A manipulable hand for laparoscopic surgery, comprising
at least one mechanical master finger, said master finger having means for releasably holding the finger of a human operator and being movable in response to movements of the finger of the operator;
a mechanical master thumb, said master thumb having means for releasably holding the thumb of the human operator and being movable in response to movements of the human thumb, said master thumb and finger being on a master control hand, said master fingers and master thumb being movably attached to a base plate of a mechanical master hand, whereby movements of each said master finger and master thumb are controlled by movements of homologous digits of the human operator hand;
motion transmission means attached to each of said master fingers and said master thumb for transmitting movements of said master finger and master thumb to a controlled slave hand,
at least one mechanical slave finger connected to and responsive to movements of said motion transmission means, said slave finger being mounted on said slave hand;

a mechanical slave thumb connected to and responsive to movements of said motion transmission means, said slave thumb being mounted on said slave hand, said movements of said motion transmission means being actuated and responsive to movements of said master fingers and said master thumb, whereby each master finger and each master thumb are connected by said motion transmission means to a homologous slave finger and slave thumb, said slave fingers and said slave thumb being mounted on a base plate of said slave hand;

a hollow elongated shaft having a longitudinal axis and proximal and distal ends, said proximal end attached to said master hand by means of a first wrist, said distal end attached to said slave hand by means of a second wrist, said wrists being hingedly movable in response to movements of said operator hand, said wrists having parallel interconnections via another of said motion transmission means, said motion transmission means passing through the hollow portion of said shaft to connect said master hand to said slave hand, said shaft having an outside diameter commensurate with insertion of said slave hand and a portion of said shaft into a cannula for use in laparoscopic surgery.

21. A manipulable hand according to claim 20, wherein each of said master fingers has at least one movable hinge and each of said slave fingers has at least one movable hinge, said hinges corresponding to interphalangeal joints of a human finger, and said slave fingers are capable of bending around an object to be grasped by movement of said hinges.

22. A manipulable hand according to claim 21, wherein said master thumb has two movable hinges and said slave thumb has two movable hinges, at least one each of said master and slave hinges corresponding to an interphalangeal joint of a human thumb, and said slave thumb is capable of bending around an object to be grasped by movement of said hinges.

23. A manipulable hand according to claim 22, wherein said master fingers have means for spreading away from and moving back towards each other, said slave fingers have means for spreading away from and moving back towards each other, and said master fingers and said slave fingers are operatively interconnected by said motion transmission means for transmittal of said spreading away from and moving back towards therebetween.

24. A manipulable hand according to claim 23, wherein said master thumb is swivelably mounted to said base plate of said master hand, whereby said master thumb is laterally swivelable for use by operators using either a right or left hand.

25. A manipulable hand according to claim 24, wherein said master hand base plate has a longitudinal axis and comprises a palm plate, said palm plate being adjustable along said longitudinal axis for varying sizes of operator hand.

26. A manipulable hand according to claim 25, wherein said shaft includes a quick connect coupling device for coupling and uncoupling a distal portion of said shaft and said slave hand from a proximal portion of said shaft and said master hand, said coupling device including means for coupling and uncoupling said motion transmission means passing through said shaft.

27. A manipulable hand according to claim 26, wherein said wrists each comprise a pivot point offset from a central axis of said shaft and an articulation point, said motion transmission means being operably attached to said articulation point for movement of said wrist, said slave wrist movable in parallel response to movement of said master wrist transmitted by said motion transmission means.

* * * * *